United States Patent
Van Der Lely et al.

(10) Patent No.: US 9,550,821 B2
(45) Date of Patent: *Jan. 24, 2017

(54) MODULATION OF GHRELIN LEVELS AND GHRELIN/UNACYLATED GHRELIN RATIO USING UNACYLATED GHRELIN

(71) Applicant: ALIZÉ PHARMA SAS, Écully (FR)

(72) Inventors: Aart Jan Van Der Lely, Bergschenhoek (NL); Thierry Abribat, Ste-Foy-les-Lyon (FR)

(73) Assignee: Alize Pharma SAS, Ecully (FR)

( * ) Notice: Subject to any disclaimer, the term of this patent is extended or adjusted under 35 U.S.C. 154(b) by 239 days.

This patent is subject to a terminal disclaimer.

(21) Appl. No.: 13/715,550

(22) Filed: Dec. 14, 2012

(65) Prior Publication Data

US 2013/0157936 A1 Jun. 20, 2013

(51) Int. Cl.

| | | |
|---|---|---|
| A61K 38/00 | (2006.01) | |
| A61P 3/04 | (2006.01) | |
| C07K 14/575 | (2006.01) | |
| A61K 38/25 | (2006.01) | |
| A61K 38/08 | (2006.01) | |
| A61K 38/22 | (2006.01) | |
| G01N 33/74 | (2006.01) | |
| C07K 5/10 | (2006.01) | |
| C07K 7/06 | (2006.01) | |
| C07K 7/08 | (2006.01) | |

(52) U.S. Cl.
CPC ............ *C07K 14/575* (2013.01); *A61K 38/08* (2013.01); *A61K 38/2264* (2013.01); *A61K 38/25* (2013.01); *C07K 5/10* (2013.01); *C07K 7/06* (2013.01); *C07K 7/08* (2013.01); *G01N 33/74* (2013.01); *G01N 2333/62* (2013.01); *G01N 2800/042* (2013.01); *G01N 2800/044* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,271,198 B1 | 8/2001 | Braisted et al. |
| 6,627,729 B1 | 9/2003 | Sheppard et al. |
| 6,872,548 B2 | 3/2005 | Coleman et al. |
| 6,967,237 B2 | 11/2005 | Bednarek |
| 7,485,620 B2 | 2/2009 | Ghigo et al. |
| 7,666,833 B2 | 2/2010 | Ghigo et al. |
| 7,825,090 B2 | 11/2010 | Ghigo et al. |
| 8,071,368 B2 | 12/2011 | Ghigo et al. |
| 8,222,217 B2 | 7/2012 | Ghigo et al. |
| 8,318,664 B2 | 11/2012 | Van Der Lely |
| 8,476,408 B2 * | 7/2013 | Brizzi et al. ............... 530/328 |
| 2005/0080007 A1 | 4/2005 | Ghigo et al. |
| 2008/0159991 A1 | 7/2008 | Ghigo et al. |
| 2008/0312133 A1 * | 12/2008 | Ghigo ................ C07K 14/60 514/1.1 |
| 2010/0016226 A1 | 1/2010 | Brizzi et al. |
| 2011/0245160 A1 * | 10/2011 | Van Der Lely ................ 514/4.9 |
| 2013/0157936 A1 | 6/2013 | Van Der Lely et al. |

FOREIGN PATENT DOCUMENTS

| | | |
|---|---|---|
| CA | 2470235 | 6/2003 |
| CA | 2471879 | 11/2003 |
| CA | 2543507 | 5/2005 |
| EP | 2067481 | 6/2009 |
| WO | WO0023469 | 4/2000 |
| WO | WO0156592 | 8/2001 |
| WO | WO0187335 | 11/2001 |
| WO | WO0192292 | 12/2001 |
| WO | WO02060472 | 8/2002 |
| WO | WO03051389 | 6/2003 |
| WO | WO2005039624 | 5/2005 |
| WO | WO 2005039624 A1 * | 5/2005 |
| WO | WO2006045319 | 5/2006 |
| WO | WO2007126792 | 11/2007 |
| WO | WO2008145749 | 12/2008 |
| WO | WO 2008145749 A1 * | 12/2008 |
| WO | WO2008145749 A1 | 12/2008 |
| WO | WO2009071283 | 6/2009 |
| WO | WO 2009071283 A2 * | 6/2009 |
| WO | WO2009150214 | 12/2009 |

(Continued)

OTHER PUBLICATIONS

Bowie et al. Deciphering the Message in Protein Sequences: Tolerance to Amino Acid Substitutions.Science, 247:1306- 1310, 1990.*
Whisstock et al. Prediction of proteinfunction fromprotein sequence and structure. Quarterly Reviews in Biophysics. 36(3):307-340, 2007.*
Lazar et al. Transforming Growth Factor alpha: Mutation of Aspartic Acid 47 and Leucine 48 Results in Different Biological Activities. Molecular and Cellular Biology. 1988. 8(3): 1247-1252.*
Stengel et al. Des-acyl ghrelin suppresses foodi ntake and body weight gain in adult obese Zucker rats. Gastroenterology. 2008. 134 (4, supplement 1): A148).*
Cummings et al. Elevated plasma ghrelin levels in Prader—Willi syndrome. Nature Medicine, 2002; 8(7): 643-644.*
Ishii et al. Role of ghrelin in streptozotocin-induced diabetic hyperphagia. Endocrinology. 2002; 143(12):4934-4937.*

(Continued)

*Primary Examiner* — Vanessa L Ford
*Assistant Examiner* — Sandra Dillahunt
(74) *Attorney, Agent, or Firm* — Fish & Richardson P.C.

(57) ABSTRACT

A method and a composition for decreasing ghrelin levels and/or decreasing ghrelin/unacylated ghrelin ratio in a subject, the method comprising administering an effective amount of unacylated ghrelin, a fragment thereof, an analog thereof and/or pharmaceutically acceptable salts thereof to the subject wherein a reduction in ghrelin levels and/or a reduction in ghrelin/unacylated ghrelin ratio is beneficial to the subject. Also, use of ghrelin level and/or ghrelin/unacylated ghrelin ratio as biomarkers for determining a subject's likelihood of responding to and/or benefiting from administration of unacylated ghrelin.

3 Claims, 12 Drawing Sheets

(56) References Cited

FOREIGN PATENT DOCUMENTS

| WO | WO2009150214 A2 | 12/2009 |
|---|---|---|
| WO | WO2013088241 | 6/2013 |

OTHER PUBLICATIONS

Cummings et al. Elevated plasma ghrelin levels in Prader-Willi syndrome. Nature Medicine, 2002; 8(7): 643-644.*
Tschop, M., et al., Ghrelin induces adiposity in rodents. Nature, 407(6806):908-913, (2000).
Van Der Lely, A.J., et al., Biological, physiological, pathophysiological, and pharmacological aspects of ghrelin., Endocr Rev, 25:426-457 (2004).
Wells, James A., Additivity of Mutational Effects in Proteins, Biochemistry, vol. 29, No. 27, Sep. 18, pp. 8509-8517, (1990).
Zhang, W, et al.; Effect of Des-Acyl Ghrelin on Adiposity and Glucose Metabolism., Endocrinology, 149:4710-4716, (2008).
PubMed Health Encyclopedia (obesity); http://www.ncbi.nlm.nih.gov/pubmedhealth/PMH0004552/ (2012).
PubMed Health Encyclopedia (diabetes); http://www.ncbi.nlm.nih.gov/pubmedhealth/PMH0002194 (2012).
Gauna et al., "Unacylated ghrelin is active on the INS-1E rat insulinoma cell line independently of the growth hormone secretagogue receptor type 1a and the corticotropin releasing factor 2 receptor," Molecular and Cellular Endocrinology; 251 (2006) pp. 103-111.
PubMed Health Encyclopedia (dyslipidemia); http://www.ncbi.nlm.nih.gov/pubmedhealth/PMH0001440/(2012).
Office Action mailed Feb. 26, 2013, which issued in U.S. Appl. No. 12/600,407.
Adelhorst, Kim, et al., Structure-Activity Studies of Glucagon-like Peptide-1, The Journal of Biological Chemistry, vol. 269, No. 9, pp. 6275-6278, (1994).
Ariyasu, H., et al.; Stomach is a major source of circulating ghrelin, and feeding state determines plasma ghrelin-like immunoreactivity levels in humans, J Clin Endocrinol Metab., 86(10):4753-8 (2001).
Asakawa, A., et al., Stomach regulates energy balance via acylated ghrelin and desacyl ghrelin, Gut., 54(1):18-24 (2005).
Atkinson, Mark A. et al., Type 1 diabetes: new perspectives on disease pathogenesis and treatment, The Lancet, vol. 358, pp. 221-229, (2001).
Baldanzi, G. et al., Ghrelin and des-acyl ghrelin inhibit cell death in cardiomyocytes and endothelial cells through ERK1/2 and PI 3-kinase/AKT., J. Cell Biol, 159:1029-1037, (2002).
Barazzoni, R., et al., Relationships between desacylated and acylated ghrelin and insulin sensitivity in the metabolic syndrome., J Clin Endocrinol Metab., Oct.;92(10):3935-40 (2007).
Broglio, F., et al., Non-Acylated Ghrelin Counteracts the Metabolic but not the Neuroendocrine Response to Acylated Ghrelin in Humans, The J. of Clinical Endocrinology & Metabolism, 89(6), pp. 3062-3065, (2004).
Broglio, F., et al.,. The endocrine response to acute ghrelin administration is blunted in patients with anorexia nervosa, a ghrelin hypersecretory state., Clin Endocrinol, (Oxf) 60(5):592-599, (2004).
Cassoni, Paola, et al., Identification, Characterization, and Biological Activity of Specific Receptors for Natural (Ghrelin) and Synthetic Growth Secretagogues and Analogs in Human Breast Carcinomas and Cell Lines., The J. of Clin. Endo. & Meta., vol. 86, pp. 1738-1745, (2001).
Cummings, D.E., et al., Elevated plasma ghrelin levels in Prader Willi syndrome., Nat Med, 8(7):643-644 (2002).
Cummings, D.E., et al., Plasma ghrelin levels after diet-induced weight loss or gastric bypass surgery., N Engl J Med., May 23;346(21):1623-30 (2002).
Date, Y., et al., The role of the gastric afferent vagal nerve in ghrelin-induced feeding and growth hormone secretion in rats., Gastroenterology, 123(4):1120-1128, (2002).

Del Rincon Jerero, J.P., Ghrelina, un peptido modulador del metabolismo energetico, Revista de endocrinologia y Nutricion, 15:138-148, (2007).
Delhanty, P, et al.; Unacylated Ghrelin Rapidly Modulates Lipogenic and Insulin Signaling Pathway Gene Expression in Metabolically Active Tissues of GHSR Deleted Mice., PloS ONE, Jun.; 5(7): 311749, (2010).
Florez, Jose C., The Genetics of Type 2 Diabetes: A Realistic Appraisal in 2008, J. Clin. Endocrinal Metab., 93(12), pp. 4633-4642, (2008).
Gauna, C. et al., Administration of acylated ghrelin reduces insulin sensitivity, whereas the combination of acylated plus unacylated ghrelin strongly improves insulin sensitivity. J Clin Endocrinol Metab., Oct.;89(10):5035-42 (2004).
Gauna, C., et al., Unacylated ghrelin acts as a potent insulin secretagogue in glucose-stimulated conditions. Am J Physiol Endocrinol Metab, 293:E697-704 (2007).
Gauna, C., et al., Ghrelin stimulates, whereas des-octanoyl ghrelin inhibits, glucose output by primary hepatocytes., Journal of Clinical Endocrinology and Metabolism, 90:1055-1060 (2005).
Gnanapavan, S., et al.; The tissue distribution of the mRNA of ghrelin and subtypes of its receptor, GHS-R, in humans, J. Clin. Endocrinol. Metab. 87:2988-2991 (2002).
Granata, R., et al., Obestatin promotes survival of pancreatic beta-cells and human islets and induces expression of genes involved in the regulation of beta-cell mass and function. Diabetes, 57:967-979 (2008).
Granata, Riccarda, et al., Acylated and unacylated ghrelin promote proliferation and inhibit serum starvation—and cytokine induced apoptosis of pancea b-cells through cAMP/PKA, ERK1/2 and PL3K/Akt., abstract and poster from Endocrine Society Meeting, Boston, Jun. 24-27, 2006.
Granata, Riccarda, et al., Acylated and Unacylated Ghrelin Promote Proliferation and Inhibit Apoptosis of Pancreatic b-cells and Human Islets: Involvment of 3', 5' Cyclic Adenosine Monophosphate/Protein Kinase A, Extracellular Signal-Regulated Kinase 1/2 and Phosphadityl Inositol 3-KinaselAkt Signaling., Endocrinology, 148(2), pp. 512-529, (2007).
Gualillo, O., et al., Introducing GOAT: a target for obesity and anti-diabetic drugs?, Trends Pharmacol Sci, 29 (8):398-401 (2008).
Haqq, A.M.F., et al., Serum ghrelin levels are inversely correlated with body mass index, age, and insulin concentrations in normal children and are markedly increased in Prader-Willi syndrome., J Clin Endocrinol Metab, 88 (1):174-178 (2003).
Hillman, J.B., et al., Ghrelin biology and its role in weight-related disorders., Discov Med., Jun.;11(61):521-8 (2011).
Howard, A.D., et al.; A receptor in pituitary and hypothalamus that functions in growth hormone release., Science, 273:974-977 (1996).
Kiewiet, R.M., et al., Effects of acute administratio of acylated and unacylated ghrelin on glucose and insulin concentratios in morbidly obese subjects without overt diabetes., Eur J Endocrinol, 161:567-573 (2009).
Kitamura, S., et al., Ghrelin concentration in cord and neonatal blood: relation to fetal growth and energy balance., J Clin Endocrinol Metab., 88(11):5473-7, (2003).
Kojima, M., et al.; Ghrelin is a growth-hormone-releasing acylated peptide from stomach, Nature, 402:656-660 (1999).
Kumar, R., et al., Proghrelin peptides: Desacyl ghrelin is a powerful inhibitor of acylated ghrelin, likely to impair physiological effects of acyl ghrelin but not of obestatin A study of pancreatic polypeptide secretion from mouse islets., Regul Pept., Sep. 24;164(2-3):65-70 (2010).
Li et al., Cardiopretective effects of ghrelin and des-octanyol ghrelin on myocardial injury induced by isoproterenol in rats, Acta Pharmacologia Sinica, 27:527-535, (2006).
Longo, K.A., et al., Improved insulin sensitivity and metabolic flexibility in ghrelin receptor knockout mice., Regul Pept, 150:55-61 (2008).
Makino et al., Semisynthesis of Human Ghrelin : Condensation of a Boc-Protected Recombinant Peptide with a Synthetic O-Acylated Fragment, Biopolymers, 79: 238-247, (2005).

(56) References Cited

OTHER PUBLICATIONS

Marzullo, Paolo, et al., The Relationship between Active Ghrelin Levels and Human Obesity involves Alteration in Resting Energy Expediture., The J. of Clinical Endocrinology & Metabolism, 89(2), pp. 936-939, (2004).
Mickle, John E., Ph.D. et al., Genotype-Phenotype Relationship in Cystic Fibrosis, Inherited Diseases of the Pancreas, vol. 84, No. 3, pp. 597-607 (2000).
Mifune, H., et al., Increased production of active ghrelin is relevant to hyperphagia in nonobese spontaneously diabetic Toni rats., Metabolism, Oct. 14, 2011 [Epub ahead of print].
Misra, M., et al., Secretory dynamics of ghrelin in adolescent girls with anorexia nervosa and healthy adolescents., Am J Physiol Endocrinol Metab, 289(2):E347-E356 (2005).
Nikolopoulos, D., et al., Ghrelin: a potential therapeutic target for cancer., Regul Pept, 163(1-3):7-17 (2010).
Nonogaki, K., et al., Hyperphagia alters expression of hypothalamic 5-HT2C and 5-HT1B receptor genes and plasma des-acyl ghrelin levels in Ay mice., Endocrinology, 147:5893-5900 (2006).
Pacifico, L. et al., Acylated and nonacylated ghrelin levels and their associations with insulin resistance in obese and normal weight children with metabolic syndrome., Eur J Endocrinol., Dec.; 161(6):861-70 (2009).
Poykko, Seppo M. et al., Low Plasma Ghrelin is Associated With Insulin Resistance, Hypertension, and the Prevalence of Type 2 Diabetes., Diabetes, vol. 52, pp. 2546-2553, (2003).
Prodam, Flavia, et al., Unacylated ghrelin (UAG) enhances the early insulin response to meal improves glucose metabolism and decrease free fatty acids levels in healthy volunteers., abstract and poster from EP Congress of Endocrinology, Budapest, Apr. 28-May 2, 2007.
Rodríguez, A., et al., Acylated and desacyl ghrelin stimulate lipid accumulation in human visceral adipocytes., Int J Obes, (Lond), 33(5):541-52 (2009).
Salehi et al., Effects of ghrelin on insulin and glucagon secretion: a study of isolated pancreatic islets and intact mice, Regulatory Peptides, 118, pp. 143-150, (2004).
Schellekens, H., et al., Lean mean fat reducing ghrelin machine: Hypothalamic ghrelin and ghrelin receptors as therapeutic targets in obesity., Neuropharmacology, 58(1):2-19 (2010).
Soares, Joao-Bruno et al., Ghrelin, des-acyl ghrelin and obestatin: Three pieces of the same puzzle, Elsevier, Peptides, 29 (2008) pp. 1255-1270, (2008).
St-Pierre, D.H., et al. Association of acylated and nonacylated ghrelin with insulin sensitivity in overweight and obese postmenopausal women., J Clin Endocrinol Metab., 92(1):264-9 (2007).
Sumithran, P., et al., Long-term persistence of hormonal adaptations to weight loss., N Engl J Med.; 365(17):1597-604 (2011).
Tong, J., et al., Ghrelin suppresses glucose-stimulated insulin secretion and deteriorates glucose tolerance in healthy humans., Diabetes, Sep.;59(9):2145-51 (2010).
Toshinai, Koji et al., Upregulation of Ghrelin Expression in the Stomach upon Fasting, Insulin-Induced Hypoglycemia, and Leptin Administration., Biochemical and Biophysical Rsrch. Comm., 281, pp. 1220-1225, (2001).
Ariyasu et al.; "Stomach is a major source of circulating ghrelin, and feeding state determines plasma ghrelin-like immunoreactivity levels in humans", J Clin Endocrinol Metab, 86(10):4753-8 (Oct. 2001).
Asakawa et al., "Stomach regulates energy balance via acylated ghrelin and desacyl ghrelin", Gut, 54(1):18-24 (Jan. 2005).
Baldanzi et al., "Ghrelin and des-acyl ghrelin inhibit cell death in cardiomyocytes and endothelial cells through ERK1/2 and PI 3-kinase/AKT", J Cell Biol, 159:1029-1037 (2002).
Bhat et al., "Skeletal muscle mitochondrial DNA injury in patients with unilateral peripheral arterial disease", Circulation, 99:807-812 (1999).
Bosch-Marce et al., "Effects of aging and hypoxia-inducible factor-1 activity on angiogenic cell mobilization and recovery of perfusion after limb ischemia", Circ Res., 101:1310-1318 (2007).

Broglio et al., "The endocrine response to acute ghrelin administration is blunted in patients with anorexia nervosa, a ghrelin hypersecretory state", Clin Endocrinol (Oxf), 60(5):592-599 (2004).
Broglio et al., "Non-acylated ghrelin counteracts the metabolic but not the neuroendocrine response to acylated ghrelin in humans", J Clin Endocrinol Metab, 89(6):3062-5 (Jun. 2004).
Cardinali et al., "Microrna-221 and microrna-222 modulate differentiation and maturation of skeletal muscle cells", PLoS One, 4:e7607 (2009).
Cieri et al., "Functional ability in patients with critical limb ischaemia is unaffected by successful revascularization", Eur J Vasc Endovasc Surg, 41:256-263 (2011).
Date et al., "The role of the gastric afferent vagal nerve in ghrelin-induced feeding and growth hormone secretion in rats", Gastroenterology, 123(4):1120-1128 (2002).
Delhanty et al., "Mechanisms in endocrinology: Ghrelin: the differences between acyl- and des-acyl ghrelin", Eur J Endocrinol., 167(5):601-608 (Nov. 2012).
Dentelli et al., "microRNA-222 controls neovascularization by regulating signal transducer and activator of transcription 5A expression", Arterioscler Thromb Vasc Biol., 30:1562-1568 (2010).
Dentelli et al., "IL-3 is a novel target to interfere with tumor vasculature", Oncogene, 30:4930-4940 (2011).
Filigheddu et al., "Ghrelin and des-acyl ghrelin promote differentiation and fusion of C2C12 skeletal muscle cells", Mol Biol Cell, 18:986-994 (2007).
Finkel, Radical medicine: treating ageing to cure disease, Nat Rev Mol Cell Biol, 6:971-976 (2005).
Gauna et al., "Administration of acylated ghrelin reduces insulin sensitivity, whereas the combination of acylated plus unacylated ghrelin strongly improves insulin sensitivity", J Clin Endocrinol Metab, 89(10):5035-42 (Oct. 2004).
Gauna et al., "Ghrelin stimulates, whereas des-octanoyl ghrelin inhibits, glucose output by primary hepatocytes", Journal of Clinical Endocrinology and Metabolism, 90:1055-1060 (2005).
Gauna et al., "Unacylated ghrelin acts as a potent insulin secretagogue in glucose-stimulated conditions", Am J Physiol Endocrinol Metab, 293:E697-704 (2007).
Gnanapavan et al., "The tissue distribution of the mRNA of ghrelin and subtypes of its receptor, GHS-R, in humans", J. Clin. Endocrinol. Metab. 87:2988-2991 (2002).
Granata et al., "Des-acyl ghrelin fragments and analogues promote survival of pancreatic β-cells and human pancreatic islets and prevent diabetes in streptozotocin-treated rats", J Med Chem. 55:2585-2596 (2012).
Gray et al., American Heart Association Writing Group 7. "Atherosclerotic Peripheral Vascular Disease Symposium II: lower-extremity revascularization: state of the art", Circulation, 118:2864-2872 (2008).
Greco et al., "Deregulated microRNAs in myotonic dystrophy type 2", PLoS One, 7:e39732 (2012).
Hellingman et al., "Variations in surgical procedures for hind limb ischaemia mouse models result in differences in collateral formation", Eur J Vasc Endovasc Surg, 40:796-803 (2010).
Howard et al., "A receptor in pituitary and hypothalamus that functions in growth hormone release", Science, 273:974-977 (1996).
Jones et al., "The p38alpha/beta MAPK functions as a molecular switch to activate the quiescent satellite cell", J Cell Biol, 169:105-116 (2005).
Kiewiet et al., "Effects of acute administratio of acylated and unacylated ghrelin on glucose and insulin concentratios in morbidly obese subjects without overt diabetes", Eur J Endocrinol, 161:567-573 (2009).
Kirchner et al., "Ghrelin and PYY in the regulation of energy balance and metabolism: lessons from mouse mutants", Am J Physiol Endocrinol Metab, 298:E909-919 (2010).
Kojima et al., "Ghrelin is a growth-hormone-releasing acylated peptide from stomach", Nature 402(6762):656-660 (1999).
Lear et al., "Des-acyl ghrelin has specific binding sites and different metabolic effects from ghrelin in cardiomyocytes", Endocrinology, 151:3286-3298 (2010).

(56) References Cited

OTHER PUBLICATIONS

Loffredo et al., "Oxidative-stress-mediated arterial dysfunction in patients with peripheral arterial disease", Eur Heart J, 28:608-612 (2007).
Lu et al., "Acute skeletal muscle injury: CCL2 expression by both monocytes and injured muscle is required for repair", FASEB J, 25:3344-3355 (2011).
Madamanchi et al., "Mitochondrial Dysfunction in Atherosclerosis", Circ. Res, 100:460-473 (2007).
Musaro A, Barberi L. Isolation and culture of mouse satellite cells. Methods Mol Biol, 633:101-111 (2010).
Pedersen et al., "Muscle mitochondrial function in patients with type 2 diabetes mellitus and peripheral arterial disease: implications in vascular surgery", Eur J Vasc Endovasc Surg, 8:356-364 (2009).
Pipinos et al., "The myopathy of peripheral arterial occlusive disease: Part 2. Oxidative stress, neuropathy, and shift in muscle fiber type", Vasc Endovascular Surg, 42:101-112 (2008).
Soares et al., "Ghrelin, des-acyl ghrelin and obestatin: three pieces of the same puzzle", Peptides, 29:255-1270 (2008).
Togliatto et al., "Unacylated ghrelin rescues endothelial progenitor cell function in individuals with type 2 diabetes", Diabetes,59:1016-1025 (2010).
Togliatto et al., "MIR221/MIR222-driven posttranscriptional regulation of P27KIP1 and P57KIP2 is crucial for high-glucose- and AGEmediated vascular cell damage", Diabetologia, 54:1930-1940 (2011).
Tong et al., "Ghrelin suppresses glucose-stimulated insulin secretion and deteriorates glucose tolerance in healthy humans", Diabetes 59(9):2145-51 (Sep. 2010).
Troy et al., "Coordination of satellite cell activation and self-renewal by Par-complex-dependent asymmetric activation of p38α/β MAPK Cell Stem", Cell, 11:541-553(2012).
Weitz et al., "Diagnosis and treatment of chronic arterial insufficiency of the lower extremities: a critical review", Circulation, 94:3026-3049 (1996).
Zaccagnini et al., "p66ShcA modulates tissue response to hindlimb ischemia", Circulation, 109:2917-2923 (2004).
Zaccagnini et al., "p66(ShcA) and oxidative stress modulate myogenic differentiation and SMR after hind limb ischemia", J Biol Chem, 282:31453-31459 (2007).
Zeoli et al., "Interleukin-3 promotes expansion of hemopoietic-derived CD45+ angiogenic cells and their arterial commitment via STAT5 activation", Blood, 112:350-361 (2008).
Zhao et al., "Oxidative damage pathways in relation to normal tissue injury", Br J Radiol, 80:S23-31 (2007).
Feigerlova et al., Hyperghrelinemia Precedes Obesity in Prader-Willi Syndrome, The Journal of Clinical Endocrinology & Metabolism, 93(7), Jul. 2008, pp. 2800-2805.
DelParigi et al., High Circulating Ghrelin: A Potential Cause for Hyperphagia and Obesity in Prader-WIlli Syndrome, The Journal of Clinical Endocrinology & Metabolism, 87(12), Dec. 2002, pp. 5461-5464.
Purtell et al., In Adults with Prader-Willi Syndrome, Elevated Ghrelin Levels are More Consistent with Hyperphagia than High PYY and GLP-1 Levels, Neuropeptides Aug. 2011, 45(4), pp. 301-307.
Tschop et al., Circulating Ghrelin Levels Are Decreased in Human Obesity Diabetes, Apr. 2001, vol. 50, No. 4, pp. 707-709.
Granata, R., et al., *Unacylated ghrelin and obestatin increase islet cell mass and prevent diabetes in streptozotocin-treated newborn rats*, Journal of the American heart association; Journal of Molecular Endocrinology, 45:9-17 (2010).
Katsuki, A., et al., *Circulating levels of active ghrelin is associated with abdominal adiposity, hyperinsulinemia and insulin resistance in patients with type 2 diabetes mellitus*; European Journal of Endocrinology, 151:573-577 (2004).
Poykko, S., et al., *Low Plasma Ghrelin Is Associated With Insulin Resistance, Hypertension, and the Prevalence of Type 2 Diabetes*, Diabetes, 52:2546-2553, (Oct. 2003).
Sharifi F., et al., *Acylated ghrelin and leptin concentrations in patients with type 2 diabetes mellitus, people with prediabetes and first degree relatives of patients with diabetes a comparative study*, Journal of Diabetes & Metabolic Disorders, 12:51 (2013) (6 pages).
Ueno, H., et al., *Plasma Ghrelin Concentrations in Different Clinical Stages of Diabetic Complications and Glycemic Control in Japanese Diabetics*, Endocrine Journal, 54(6):895-902 (2007).
Granata, et al., "Des-acyl Ghrelin Fragments and Analogues Promote Survival of Pancreatic [beta]-Cells and Human Pancreatic Islets and Prevent Diabetes in Streptozotocin-Treated Rats", J Med Chem, 55(6):2585-2596 (2012).
Shimada, et al. "Des-acyl ghrelin protects microvascular endothelial cells from oxidative stress-induced apoptosis through sirtuin 1 signaling pathway", Metabolism, Clinical and Experimental, 63(4):469-474 (Dec. 28, 2013).
Togliatto, et al., "Unacylated Ghrelin Rescues Endothelial Progenitor Cell Function in Individuals With Type 2 Diabetes", Diabetes; 59(4):1016-1025 (Apr. 1, 2010).
Togliatto, et al., "Unacylated Ghrelin Promotes Skeletal Muscle Regeneration Following Hindlimb Ischemia Via SOD-2-Mediated miR-221/222 Expression", J American Heart Assoc, 2(6):1-22 (Dec. 5, 2013).
International Search Report and Written Opinion for Int. App No. PCT/IB2014/001538, dated Feb. 26, 2015 (14 pages).
Alize Pharma, Unacylated Ghrelin (UAG), 2013, Retrieved from the Internet: URL:http://www.alz-pharma.com/r-and-d-projets/unacylated-ghrelinuag, retrieved on Apr. 24, 2013.
Delparigi et al., High circulating ghrelin: A potential cause for hyperphagie and obesity in Prader-Willi syndrome, J Clin Endocrinol and Metabolism, 87(12):5461-5464, Dec. 2002.
Written Opinion of the International Searching Authority mailed on Jun. 4, 2013 in connection with International Patent Application PCT/IB2012/002867 (11 pages).
International Search Report mailed Jun. 4, 2013 2013 in connection with International Patent Application PCT/IB2012/002867 (4 pages).
JP Office Action issued in JP Patent Application No. 2014-546665, dated May 17, 2016 (with English Translation) (7 pages).
Inhoff et al., *Desacyl Ghrelin Inhibits the Orexigenic Effect of Peripherally Injected Ghrelin in Rats*, Peptides, 29(12):2159-2168 (Dec. 2008).

\* cited by examiner

SEQUENCE LISTING

```
<160> NUMBER OF SEQ ID NOS: 30

<210> SEQ ID NO 1
<211> LENGTH: 28
<212> TYPE: PRT
<213> ORGANISM: Homo sapiens

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 14
<212> TYPE: PRT
<213> ORGANISM: Homo sapiens

<400> SEQUENCE: 2

Gly Ser Ser Phe Leu Ser Pro Glu His Gln Arg Val Gln Gln
1               5                   10

<210> SEQ ID NO 3
<211> LENGTH: 18
<212> TYPE: PRT
<213> ORGANISM: Homo sapiens

<400> SEQUENCE: 3

Gly Ser Ser Phe Leu Ser Pro Glu His Gln Arg Val Gln Gln Arg Lys
1               5                   10                  15

Glu Ser

<210> SEQ ID NO 4
<211> LENGTH: 5
<212> TYPE: PRT
<213> ORGANISM: Homo sapiens

<400> SEQUENCE: 4

Gly Ser Ser Phe Leu
1               5

<210> SEQ ID NO 5
<211> LENGTH: 12
<212> TYPE: PRT
<213> ORGANISM: Homo sapiens

<400> SEQUENCE: 5

Glu Ser Lys Lys Pro Pro Ala Lys Leu Gln Pro Arg
1               5                   10

<210> SEQ ID NO 6
```

```
<211> LENGTH: 8
<212> TYPE: PRT
<213> ORGANISM: Homo sapiens

<400> SEQUENCE: 6

Ser Pro Glu His Gln Arg Val Gln
1               5

<210> SEQ ID NO 7
<211> LENGTH: 6
<212> TYPE: PRT
<213> ORGANISM: Homo sapiens

<400> SEQUENCE: 7

Glu His Gln Arg Val Gln
1               5

<210> SEQ ID NO 8
<211> LENGTH: 5
<212> TYPE: PRT
<213> ORGANISM: Homo sapiens

<400> SEQUENCE: 8

Glu His Gln Arg Val
1               5

<210> SEQ ID NO 9
<211> LENGTH: 13
<212> TYPE: PRT
<213> ORGANISM: Homo sapiens

<400> SEQUENCE: 9

Ser Pro Glu His Gln Arg Val Gln Gln Arg Lys Glu Ser
1               5                   10

<210> SEQ ID NO 10
<211> LENGTH: 4
<212> TYPE: PRT
<213> ORGANISM: Homo sapiens

<400> SEQUENCE: 10

Glu His Gln Arg
1

<210> SEQ ID NO 11
<211> LENGTH: 4
<212> TYPE: PRT
<213> ORGANISM: Homo sapiens

<400> SEQUENCE: 11

His Gln Arg Val
1

<210> SEQ ID NO 12
<211> LENGTH: 8
<212> TYPE: PRT
<213> ORGANISM: Homo sapiens

<400> SEQUENCE: 12

Ser Pro Asp His Gln Arg Val Gln
1               5

<210> SEQ ID NO 13
<211> LENGTH: 8
<212> TYPE: PRT
```

<213> ORGANISM: Homo sapiens

<400> SEQUENCE: 13

Ser Pro Glu His Gln Lys Val Gln
1               5

<210> SEQ ID NO 14
<211> LENGTH: 8
<212> TYPE: PRT
<213> ORGANISM: Homo sapiens

<400> SEQUENCE: 14

Gly Pro Glu His Gln Arg Val Gln
1               5

<210> SEQ ID NO 15
<211> LENGTH: 8
<212> TYPE: PRT
<213> ORGANISM: Homo sapiens

<400> SEQUENCE: 15

Ala Pro Glu His Gln Arg Val Gln
1               5

<210> SEQ ID NO 16
<211> LENGTH: 8
<212> TYPE: PRT
<213> ORGANISM: Homo sapiens

<400> SEQUENCE: 16

Ser Ala Glu His Gln Arg Val Gln
1               5

<210> SEQ ID NO 17
<211> LENGTH: 8
<212> TYPE: PRT
<213> ORGANISM: Homo sapiens

<400> SEQUENCE: 17

Ser Pro Ala His Gln Arg Val Gln
1               5

<210> SEQ ID NO 18
<211> LENGTH: 8
<212> TYPE: PRT
<213> ORGANISM: Homo sapiens

<400> SEQUENCE: 18

Ser Pro Glu Ala Gln Arg Val Gln
1               5

<210> SEQ ID NO 19
<211> LENGTH: 8
<212> TYPE: PRT
<213> ORGANISM: Homo sapiens

<400> SEQUENCE: 19

Ser Pro Glu His Ala Arg Val Gln
1               5

<210> SEQ ID NO 20
<211> LENGTH: 8
<212> TYPE: PRT
<213> ORGANISM: Homo sapiens

```
<400> SEQUENCE: 20

Ser Pro Glu His Gln Ala Val Gln
1               5

<210> SEQ ID NO 21
<211> LENGTH: 8
<212> TYPE: PRT
<213> ORGANISM: Homo sapiens

<400> SEQUENCE: 21

Ser Pro Glu His Gln Arg Ala Gln
1               5

<210> SEQ ID NO 22
<211> LENGTH: 8
<212> TYPE: PRT
<213> ORGANISM: Homo sapiens

<400> SEQUENCE: 22

Ser Pro Glu His Gln Arg Val Ala
1               5

<210> SEQ ID NO 23
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 23

Ser Pro Glu His Gln Arg Val Gln
1               5

<210> SEQ ID NO 24
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: D-amino acid

<400> SEQUENCE: 24

Ser Pro Glu His Gln Arg Val Gln
1               5

<210> SEQ ID NO 25
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: Cyclic

<400> SEQUENCE: 25

Ser Pro Glu His Gln Arg Val Gln
1               5

<210> SEQ ID NO 26
<211> LENGTH: 8
```

```
<212> TYPE: PRT
<213> ORGANISM: Homo sapiens
<220> FEATURE:
<221> NAME/KEY: MISC_FEATURE
<222> LOCATION: (3)..(6)
<223> OTHER INFORMATION: Cyclic

<400> SEQUENCE: 26

Ser Pro Glu His Gln Lys Val Gln
1               5

<210> SEQ ID NO 27
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(6)
<223> OTHER INFORMATION: Cyclic

<400> SEQUENCE: 27

Ser Pro Glu His Gln Lys Val Gln
1               5

<210> SEQ ID NO 28
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 28

Ser Pro Glu His Gln Lys Val Gln
1               5

<210> SEQ ID NO 29
<211> LENGTH: 3
<212> TYPE: PRT
<213> ORGANISM: Homo sapiens

<400> SEQUENCE: 29

His Gln Arg
1

<210> SEQ ID NO 30
<211> LENGTH: 14
<212> TYPE: PRT
<213> ORGANISM: Homo sapiens

<400> SEQUENCE: 30

Gln Gln Val Arg Gln His Glu Pro Ser Leu Phe Ser Ser Gly
1               5                   10
```

MODULATION OF GHRELIN LEVELS AND GHRELIN/UNACYLATED GHRELIN RATIO USING UNACYLATED GHRELIN

CROSS-REFERENCE TO RELATED APPLICATIONS

This application claims the benefit of and priority to U.S. provisional patent application No. 61/576,217, filed Dec. 15, 2011, the content of which is herein incorporated by reference in its entirety.

REFERENCE TO SEQUENCE LISTING

Pursuant to 37 C.F.R. 1.82(c), a sequence listing is submitted electronically herewith via EFS Web as an ASCII compliant text file named "Sequence Listing.txt" that was created on Dec. 14, 2012, and has a size of 5051 bytes. The content of the aforementioned file named "Sequence Listing.txt" is hereby incorporated by reference in its entirety.

FIELD OF THE INVENTION

This invention relates to the use of unacylated ghrelin, fragments and/or analogs thereof for modulating ghrelin levels and/or ghrelin/unacylated ghrelin ratio in a subject wherein such modulation is beneficial to the subject. The invention also relates to the composition comprising unacylated ghrelin, fragments and/or analogs thereof modulating ghrelin levels and/or ghrelin/unacylated ghrelin ratio in a subject wherein such modulation is beneficial to the subject. The invention further relates to the use of ghrelin level and/or ghrelin/unacylated ghrelin ratio as biomarkers for determining a subject's likelihood of responding to and/or benefiting from administration of unacylated ghrelin.

BACKGROUND

Ghrelin (also referred as "acylated ghrelin" or abbreviated as "AG") is a 28 amino acid peptide, purified and identified from rat stomach and characterized by the presence of an n-octanoyl modification on the Ser3 residue (Ref. 1). Acylation of ghrelin is catalyzed by the enzyme ghrelin O-acyl transferase (GOAT). The expression of GOAT is mostly in the stomach and intestine. Ghrelin is the endogenous ligand of the growth hormone (GH) secretagogue receptor (GHSR-1a) (Refs. 2, 3). Ghrelin is now mostly recognized as a potent orexigenic factor stimulating food intake and modulating energy expenditure (Refs. 4, 5 and 6). At the peripheral level, Ghrelin exerts probably its major physiological action regulating glucose and lipid metabolism (Ref. 7). In fact, ghrelin has a diabetogenic action (Ref. 8) and suppresses glucose-stimulated insulin secretion and deteriorates glucose tolerance (Ref. 9).

As such, elevated plasma ghrelin is of relevance in certain disorders of the metabolism and growth such as in diabetes and obesity. Elevated plasma ghrelin levels have also been demonstrated amongst adults and children with Prader-Willi Syndrome (PWS) (Ref. 10 and 11). PWS is a genetic obesity syndrome associated in most patients with GH deficiency. Children with PWS present a rapid weight gain along with a voracious appetite. Studies on the involvement of ghrelin in PWS have provided a significant rationale that the hyperphagia observed in PWS is positively correlated with elevated ghrelin levels, consistent with the known orexigenic effect of ghrelin (Ref. 12).

Unacylated ghrelin (also referred as "des-acyl ghrelin" or abbreviated as "UAG"), is the non-acylated form of ghrelin. Its concentration in plasma and tissue is higher compared to ghrelin. UAG has long been considered as a product with no physiological role as it fails to bind the only known ghrelin receptor GHSR-1a at physiological concentrations and has no physiological effect on GH secretion (Ref. 15). However, UAG is a biologically active peptide, particularly at the metabolic level and its administration has been shown to induce a negative energy balance by decreasing food intake and delaying gastric emptying (Ref. 16). Over-expression of UAG in mice results in a decrease in fat accumulation with an increase in insulin sensitivity and glucose tolerance (Refs. 16 and 17).

UAG has been shown to prevent the hyperglycemic effects of ghrelin, when administered concomitantly, in healthy volunteers, see in particular U.S. Pat. No. 7,825,090, herein incorporated in its entirety by reference. This initial observation was followed by several reports on the anti-diabetogenic potential of UAG (Refs. 18, 19, 30, 31 and 32).

In vitro, in vivo and clinical evidence indicate that UAG prevents the diabetogenic effects of ghrelin in healthy volunteers and in GH-deficient patients (Refs. 18 and 19). It inhibits both basal and ghrelin-induced glucose secretion by human hepatocytes (Ref. 31). In rats, UAG enhances portal insulin response to glucose (Ref. 32) and reduces fat deposition and triglycerides levels, as observed in transgenic mice overexpressing UAG (Ref. 16). In vitro, UAG stimulates insulin secretion from insulinoma cells (Ref. 32) and promotes proliferation and inhibits apoptosis of beta cells (Ref. 33).

The anti-diabetogenic effects and ghrelin-antagonizing effects of UAG, fragments and analogs thereof have been reported in U.S. Pat. No. 7,485,620; U.S. Pat. No. 8,222, 217; U.S. Pat. No. 8,318,664 and in WO 2008/145749, which are all in their entirety incorporated herein by reference.

Recent experiments on circulating angiogenic cells (CAC) indicates that UAG beneficially impacts the vascular remodeling process which is known to be impaired in type 2 diabetes patients. The effects of UAG on CAC have been reported in U.S. Patent Application Serial Number 2010/0016226 and in WO 2009/150214, herein incorporated in their entirety by reference.

Obese mice and humans have been reported to present lower UAG levels than normal weight subjects, indicating that obesity might be correlated with a relative UAG deficiency (Refs. 34, 35 and 21). It has been observed that insulin-resistant obese subjects have an elevated AG/UAG ratio when compared to insulin-sensitive obese subjects (Refs. 20 and 22).

Treatments that target ghrelin and the GHS-R (i.e., ghrelin antagonists) have been suggested as attractive pharmacologic avenues to fight against obesity and other conditions, disorders and diseases associated with ghrelin. Several GHS-R ligands and anti-obesity vaccines have been proposed (Ref. 24). Other pharmacological approaches inducing antibodies against ghrelin, ghrelin enantiomers and inhibition of ghrelin acyl-transferase (GOAT) (Ref. 25) have been investigated; however, due to lack of efficacy, non-selectivity and lack of sustained weight loss, these pharmacological approaches have not yet reached the market (Ref. 26).

Therefore, there exists a need in the art for an efficient and more direct way of modulating circulating ghrelin levels and/or circulating ghrelin/unacylated ghrelin ratio in subjects wherein such modulation is beneficial to the subject and for more efficient ways of identifying those subjects that can benefit from modulation of ghrelin levels and ghrelin/unacylated ghrelin ratio.

SUMMARY OF THE INVENTION

According to one aspect, the present invention provides a method for decreasing ghrelin levels in a subject, comprising administering an effective amount of unacylated ghrelin, a fragment thereof, an analog thereof and/or pharmaceutically acceptable salts thereof to the subject.

According to another aspect, the present invention provides a method for decreasing ghrelin levels and ghrelin/unacylated ghrelin ratio in a subject, comprising administering an effective amount of unacylated ghrelin, a fragment thereof, an analog thereof and/or pharmaceutically acceptable salts thereof to the subject.

According to another aspect, the present invention provides a method for ameliorating a symptom associated with ghrelin levels in a subject, comprising administering an effective amount of unacylated ghrelin, a fragment thereof, an analog thereof and/or pharmaceutically acceptable salts thereof to the subject.

According to another aspect, the present invention provides a method for ameliorating a symptom associated with ghrelin levels and with ghrelin/unacylated ghrelin ratio in a subject, comprising administering an effective amount of unacylated ghrelin, a fragment thereof, an analog thereof and/or pharmaceutically acceptable salts thereof to the subject.

According to another aspect, the present invention provides a method for ameliorating and/or treating a condition caused by elevated ghrelin levels in a subject, comprising administering to a subject having the condition an effective amount of unacylated ghrelin, a fragment thereof, an analog thereof and/or pharmaceutically acceptable salts thereof.

According to another aspect, the present invention provides a method for ameliorating and/or treating a condition cause by elevated ghrelin levels and elevated ghrelin/unacylated ghrelin ratio in a subject, comprising administering to a subject having the condition an effective amount of unacylated ghrelin, a fragment thereof, an analog thereof and/or pharmaceutically acceptable salts thereof.

According to another aspect, the present invention provides a method for preventing weight gain in a subject following diet-induced weight loss, comprising administering an effective amount of unacylated ghrelin, a fragment thereof, an analog thereof and/or pharmaceutically acceptable salts thereof to the subject.

According to another aspect, the present invention provides a pharmaceutical composition comprising an effective amount of unacylated ghrelin, a fragment thereof, an analog thereof and/or pharmaceutically acceptable salts thereof and a pharmaceutically acceptable diluent for decreasing ghrelin levels in a subject.

According to another aspect, the present invention provides a pharmaceutical composition comprising an effective amount of unacylated ghrelin, a fragment thereof, an analog thereof and/or pharmaceutically acceptable salts thereof and a pharmaceutically acceptable diluent for ameliorating symptoms associated with ghrelin levels in a subject.

According to another aspect, the present invention provides a pharmaceutical composition comprising an effective amount of unacylated ghrelin, a fragment thereof, an analog thereof and/or pharmaceutically acceptable salts thereof and a pharmaceutically acceptable diluent for preventing weight gain in a subject following diet-induced weight loss.

According to another aspect, the present invention provides the use of an effective amount of unacylated ghrelin, a fragment thereof, an analog thereof and/or pharmaceutically acceptable salts thereof and a pharmaceutically acceptable diluent for decreasing ghrelin levels in a subject.

According to another aspect, the present invention provides the use of an effective amount of unacylated ghrelin, a fragment thereof, an analog thereof and/or pharmaceutically acceptable salts thereof and a pharmaceutically acceptable diluent for ameliorating symptoms associated with ghrelin levels in a subject.

According to another aspect, the present invention provides the use of an effective amount of unacylated ghrelin, a fragment thereof, an analog thereof and/or pharmaceutically acceptable salts thereof and a pharmaceutically acceptable diluent for preventing weight gain in a subject following diet-induced weight loss.

According to another aspect, the present invention provides a method for screening within a population of subjects suffering from diabetes, Prader-Willi Syndrome, obesity, insulin resistance or hyperphagia, which subjects within the population are susceptible of benefiting from an administration of unacylated ghrelin, a fragment thereof or an analog thereof, comprising: determining a level of circulating ghrelin from the subjects of the population; processing the level of circulating ghrelin at least in part based on a reference level of circulating ghrelin to derive information conveying whether the level of circulating ghrelin is elevated; and causing conveyance of the information to a recipient for determining the subject's susceptibility of benefiting from administration of unacylated ghrelin.

According to another aspect, the present invention provides a method for screening within a population of subjects suffering from diabetes, Prader-Willi Syndrome, obesity, insulin resistance or hyperphagia, which subjects are susceptible of benefiting from an administration of unacylated ghrelin, a fragment thereof or an analog thereof, comprising: determining a level of circulating ghrelin and a ratio of circulating ghrelin/unacylated ghrelin from the subjects of the population; processing the level of circulating ghrelin and the ratio of circulating ghrelin/unacylated ghrelin at least in part based on a reference level of circulating ghrelin and a reference ratio of circulating ghrelin/unacylated ghrelin to derive information conveying whether the level of circulating ghrelin and the ratio of circulating ghrelin/unacylated ghrelin are elevated; and causing conveyance of the information to a recipient for determining the subject's susceptibility of benefiting from administration of unacylated ghrelin.

BRIEF DESCRIPTION OF THE FIGURES

In FIG. 2A, AG serum levels in pg/ml were measured following placebo or UAG administration before and one hour after SBM. In FIG. 2B, UAG serum levels in pg/ml were measured following placebo or UAG administration before and one hour after SBM.

FIG. 3A shows the mean absolute glucose levels after SBM and following placebo, UAG 3 mcg/kg/h and UAG 10 mcg/kg/h infusions. Repeated measures ANOVA p<0.0001; Bonferroni's Multiple Comparisons placebo vs. 3 mcg NS; placebo vs. 10 mcg p<0.001; 3 mcg vs. 10 mcg p<0.001. FIG. 3B shows the mean t0-t180 glucose levels for the three treated groups.

FIG. 4A shows the change in glucose levels from pre-meal baseline following placebo, UAG 3 mcg/kg/h and UAG 10 mcg/kg/h infusions. Repeated measures ANOVA p<0.0001; Bonferroni's Multiple Comparisons placebo vs. 3 mcg p<0.001; placebo vs. 10 mcg p<0.001; 3 mcg vs. 10 mcg p<0.05. FIG. 4B shows the mean t0-t180 glucose levels for the three treated groups.

FIG. 7C shows circulating AG levels before UAG infusion and following a 2.5 hour UAG infusion. FIG. 7D shows the AG change from baseline after a 2.5 hour UAG infusion ([AG] level at 12:00–[AG] levels at 9:30). Two-tailed Wilcoxon matched-pairs signed rank test; *: p<0.05; **: p<0.01.

DETAILED DESCRIPTION

Figure 1:
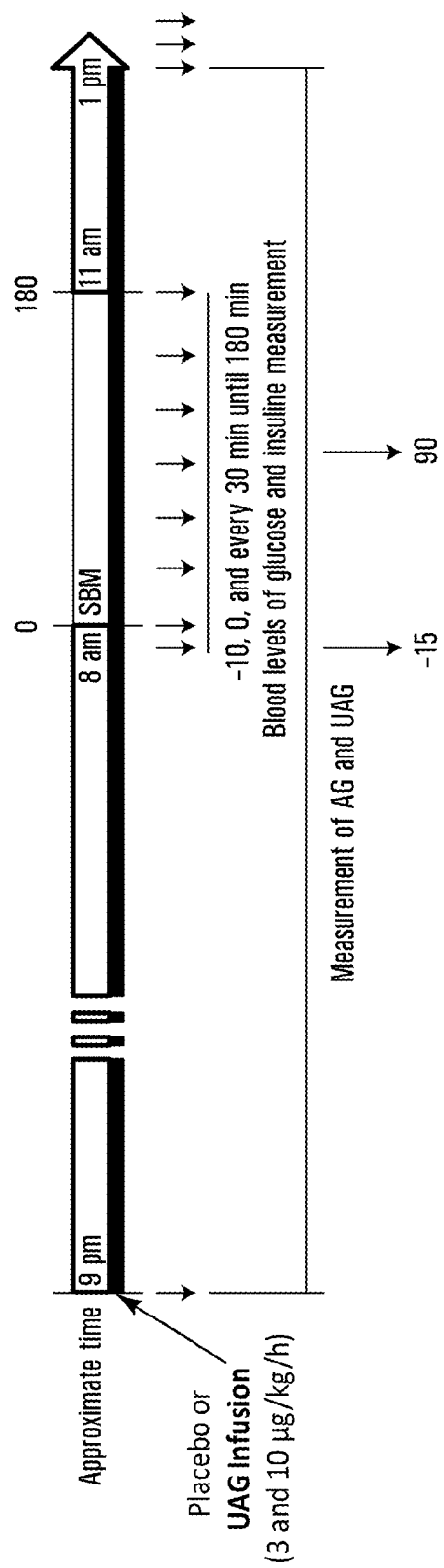
FIG. 1 is a schematic representation of a study protocol involving Type 2 Diabetes Mellitus (T2DM) subjects according to one embodiment of the present invention. SBM refers to Standard Breakfast Meal.

The present invention stems from, but is not limited to, the findings by the Inventors that administration of UAG decreases levels of circulating AG in subjects with T2DM. The present invention further stems from the findings that the higher the level of basal AG, the more important are the effects of UAG on reducing AG levels and on reducing the deleterious effects associated with AG levels such as, for example, obesity, hyperglycemia, insulin resistance, fat deposition, hyperphagia and obesity associated with insulin resistance.

The Inventors have also found that the higher the ratio of circulating AG/UAG, the more efficient is UAG in decreasing such ratio and in suppressing the deleterious effects associated with AG/UAG ratio.

In view of this, circulating AG level and circulating AG/UAG ratio may each be used as biomarkers for identifying a subject's likelihood of responding to and/or benefiting from administration of UAG. These biomarkers may thus be used for identifying within a population of subjects suffering from a condition such as, but not limited to, obesity, diabetes, insulin resistance, Prader-Willi, hyperphagia and hyperghrelinemia, which of the subjects are likely to respond to and/or benefit from administration of UAG. The higher the circulating AG levels and/or the higher the circulating AG/UAG ratio in a subject, the more this subject is likely to respond to and/or benefit from the administration of UAG.

To this date, studies have reported that UAG counteracts the peripheral actions of ghrelin on, for example, glucose and insulin metabolisms. The present study provides the first evidence that administration of UAG also suppresses circulating ghrelin levels and provides the first evidence of the existence of a correlation between the level of circulating AG and the efficacy of UAG in improving metabolic parameters affected by AG levels and/or by AG/UAG ratio.

The surprising demonstrations presented therein allow to expand the applications and the indications for which unacylated ghrelin can be used so as to include the facilitation, amelioration and/or treatment of conditions that result from AG levels and/or AG/UAG ratio.

These demonstrations also allow to expand the applications and the indications for which unacylated ghrelin can be used so as to include the facilitation, amelioration and/or treatment of conditions that result from elevated AG levels and/or elevated AG/UAG ratio.

As used herein, the expression "elevated AG level(s)" refers to a level of circulating AG that is above the AG level observed in normal and/or healthy subjects. In some implementations, the expression "elevated AG level(s)" refers to a level of circulating AG at which one or more deleterious physiological symptoms associated with AG appear, persist or are worsen in a subject.

As used herein, the expression "elevated AG/UAG ratio" refers to a ratio of circulating AG/UAG that is above the AG/UAG ratio observed in normal and/or healthy subjects.

In some implementations, the expression "elevated AG/UAG ratio" refers to a ratio of circulating AG/UAG at which one or more deleterious physiological symptoms associated with the AG/UAG ratio appear or persist or are worsen in a subject.

It is to be understood that several factors may affect the levels of circulating ghrelin and unacylated ghrelin in normal subjects. Examples of such factors include, but are not limited to, gender, age, fitness, body mass index (BMI), eating habits, etc.

As used herein, the expression "inhibition of ghrelin" refers to an impairment of the biological activity of ghrelin which occurs due to a decrease in ghrelin levels and/or due to an impairment of its biological activity.

A person skilled in the art will be familiar with the techniques and assays for measuring AG and UAG levels in a subject. Such techniques may include techniques that involve the use of protease inhibitors such as 4-(2-aminoethyl)benzenesulfonyl fluoride hydrochloride (AEBSF) or other cocktail of protease inhibitors.

In one implementation of this embodiment, an obese subject is characterized as having a body weight approximately 20%, approximately 25%, approximately 30% or greater than the normal body weight for said subject. Normal body weight may be determined by a comparison of the weight of the subject at a prior point in time, such as when AG levels were normal and/or when AG/UAG ratio was normal, or by a comparison of the AG levels and/or AG/UAG ratio of the subject as compared to averages of other subjects of a similar age and/or condition.

In another implementation of this embodiment, an overweight subject is characterized as having a body weight approximately 5% greater to approximately 20% greater than the normal body weight for said subject. Normal body weight may be determined by a comparison of the weight of the subject at a prior point in time, such as when AG levels were normal and/or when AG/UAG ratio was normal, or by a comparison of the AG levels and/or AG/UAG ratio as compared to averages of other subjects of a similar age and/or condition.

In another implementation of this embodiment, a normal subject is characterized as having a body weight approximately 5% greater than to approximately 5% less than the normal body weight for said subject. Normal body weight may be determined by a comparison of the weight of the subject at a prior point in time, such as when AG levels were normal and/or when AG/UAG ratio was normal, or by a comparison of the AG levels and/or AG/UAG ratio as compared to averages of other subjects of a similar age and/or condition. A normal weight subject may have a BMI in the approximate range of 19-22.

Unless defined otherwise, all technical and scientific terms used herein have the same meaning as commonly understood by one of skill in the art to which the invention pertains.

i) Unacylated Ghrelin, Fragments and Analogs Thereof

The terms "unacylated ghrelin", "des-acyl ghrelin" and the abbreviation "UAG" are intended to mean peptides that have the amino acid sequence specified in SEQ ID NO: 1 which amino acid sequence is:

```
                                            (SEQ ID NO: 1)
Gly-Ser-Ser-Phe-Leu-Ser-Pro-Glu-His-Gln-Arg-Val-

Gln-Gln-Arg-Lys-Glu-Ser-Lys-Lys-Pro-Pro-Ala-Lys-

Leu-Gln-Pro-Arg
```

Unacylated ghrelin may also be referred to as UAG (1-28).

Naturally-occurring variations of UAG include peptides that contain substitutions, additions or deletions of one or more amino acids which result due to discrete changes in the nucleotide sequence of the encoding ghrelin gene or alleles thereof or due to alternative splicing of the transcribed RNA. It is understood that the changes do not substantially affect the properties, pharmacological and biological characteristics of unacylated ghrelin variants. Those peptides may be in the form of salts. Particularly the acidic functions of the molecule may be replaced by a salt derivative thereof such as, but not limited to, a trifluoroacetate or an acetate salt.

By "peptide", "polypeptide" or "protein" is meant any chain of amino acids, regardless of length or post-translational modification (e.g., glycosylation or phosphorylation), or chemical modification, or those containing unnatural or unusual amino acids such as D-Tyr, ornithine, amino-adipic acid. The terms are used interchangeably in the present application.

The expressions "fragments" and "fragments thereof" refer to amino acid fragments of a peptide such as UAG. Fragments of UAG are shorter than the amino acid sequence depicted in SEQ ID NO: 1, therefore are shorter than 28 amino acid residues. Fragments of UAG may therefore be 27, 26, 25, 24, 23, 22, 21, 20, 19, 18, 17, 16, 15, 14, 13, 12, 11, 10, 9, 8, 7, 6, 5 or 4 amino acid residues in length. For example, fragments of UAG may have the amino acid sequences depicted in Table 1 below:

TABLE 1

| Fragment | SEQ ID NO: | Amino Acid Sequence |
|---|---|---|
| UAG (1-14) | 2 | Gly-Ser-Ser-Phe-Leu-Ser-Pro-Glu-His-Gln-Arg-Val-Gln-Gln |
| UAG (1-18) | 3 | Gly-Ser-Ser-Phe-Leu-Ser-Pro-Glu-His-Gln-Arg-Val-Gln-Gln-Arg-Lys-Glu-Ser |
| UAG (1-5) | 4 | Gly-Ser-Ser-Phe-Leu |
| UAG (17-28) | 5 | Glu-Ser-Lys-Lys-Pro-Pro-Ala-Lys-Leu-Gln-Pro-Arg |
| UAG (6-13) | 6 | Ser-Pro-Glu-His-Gln-Arg-Val-Gln |
| UAG (8-13) | 7 | Glu-His-Gln-Arg-Val-Gln |
| UAG (8-12) | 8 | Glu-His-Gln-Arg-Val |
| UAG (6-18) | 9 | Ser-Pro-Glu-His-Gln-Arg-Val-Gln-Gln-Arg-Lys-Glu-Ser |
| UAG (8-11) | 10 | Glu-His-Gln-Arg |
| UAG (9-12) | 11 | His-Gln-Arg-Val |
| UAG (9-11) | 29 | His-Gln-Arg |
| UAG (14-1) | 30 | Gln Gln Val Arg Gln His Glu Pro Ser Leu Phe Ser Ser Gly |

Any other fragments of UAG that preserve the biological activity of UAG are encompassed by the present invention. Some UAG fragments have been reported in U.S. Pat. No. 8,222,217; U.S. Pat. No. 8,318,664 and in WO/2008/145749, incorporated herein in their entirety by reference, wherein it has been demonstrated that the smallest UAG fragment to retain the biological activity of UAG is UAG (9-12) depicted herein as SEQ ID NO: 11.

In one embodiment, the polypeptides such as UAG, fragments or analogs thereof, are used in a form that is "purified", "isolated" or "substantially pure". The polypeptides are "purified", "isolated" or "substantially pure" when they are separated from the components that naturally accompany them. Typically, a compound is substantially pure when it is at least 60%, 65%, 70%, 75%, 80%, 85%, 90%, 95%, 96%, 97%, 98%, or 99%, by weight, of the total material in a sample.

The expressions "analog of unacylated ghrelin", "analog of fragments of unacylated ghrelin" and "analogs thereof" refer to both structural and functional analogs of UAG or fragments thereof which are, inter alia, capable of replacing UAG in the biological function of UAG as described in the present application, such as, but not limited to modulate AG;

inhibit AG; decrease circulating AG levels; decrease circulating elevated AG levels; decrease circulating AG/UAG ratio; decrease circulating elevated AG/UAG ratio; ameliorate the symptoms induced by AG levels and/or AG/UAG levels; facilitate, prevent and/or treat conditions associated with circulating AG and/or circulating AG/UAG ratio and facilitate, prevent and/or treat conditions associated with elevated circulating AG and/or elevated circulating AG/UAG ratio. Some analogs of UAG have been reported in U.S. Pat. No. 8,222,217; U.S. Pat. No. 8,318,664 and in WO/2008/145749, incorporated herein in their entirety by reference.

Simple structural analogs comprise peptides showing homology with UAG as set forth in SEQ ID NO: 1 or homology with any fragment thereof. An example of an analog of AG is an isoform of Ghrelin-28, des Gln-14 Ghrelin (a 27 amino acid peptide possessing serine 3 modification by n-octanoic acid) which is shown to be present in stomach. It is functionally identical to AG in that it binds to GHSR-1a with similar binding affinity, elicits $Ca^{2+}$ fluxes in cloned cells and induces GH secretion with similar potency as Ghrelin-28. It is expected that UAG also has a des Gln-14 UAG that is functionally identical to UAG.

Preferred analogs of UAG and preferred analogs of fragments of UAG are those that vary from the native UAG sequence or from the native UAG fragment sequence by conservative amino acid substitutions; i.e., those that substitute a residue with another of like characteristics. Typical substitutions include those among Ala, Val, Leu and Ile; among Ser and Thr; among the acidic residues Asp and Glu; among Asn and Gln; among the basic residues Lys and Arg; and among the aromatic residues Phe and Tyr. Particularly preferred are analogs in which several, for example, but not limited to, 5-10, 1-5, or 1-2 amino acids are substituted, deleted, or added in any combination. For example, the analogs of UAG may differ in sequence from UAG by 1, 2, 3, 4, 5, 6, 7, 8, 9 or 10 amino acid substitutions (preferably conservative substitutions), deletions, or additions, or combinations thereof.

There are provided herein, analogs of the peptides of the invention that have at least 50%, 55%, 60%, 65%, 70%, 75%, 80%, 85%, 90%, 95%, 96%, 97%, 98% or 99% sequence homology or sequence identity with the amino acid sequences described herein over its full length, and sharing at least one of the metabolic effects or biological activity of UAG. A person skilled in the art would readily identify an analog sequence of unacylated ghrelin or an analog sequence of a fragment of unacylated ghrelin.

Examples of analogs of UAG are provided in Table 2 below:

TABLE 2

| Analog | SEQ ID NO: | Amino acid sequence |
|---|---|---|
| (Asp)8 UAG (6-13)NH$_2$ | 12 | Ser-Pro-Asp-His-Gln-Arg-Val-Gln |
| (Lys)11 UAG (6-13)NH$_2$ | 13 | Ser-Pro-Glu-His-Gln-Lys-Val-Gln |
| (Gly)6 UAG (6-13)NH$_2$ | 14 | Gly-Pro-Glu-His-Gln-Arg-Val-Gln |
| (Ala)6 UAG (6-13)NH$_2$ | 15 | Ala-Pro-Glu-His-Gln-Arg-Val-Gln |
| (Ala)7 UAG (6-13)NH$_2$ | 16 | Ser-Ala-Glu-His-Gln-Arg-Val-Gln |
| (Ala)8 UAG (6-13)NH$_2$ | 17 | Ser-Pro-Ala-His-Gln-Arg-Val-Gln |
| (Ala)9 UAG (6-13)NH$_2$ | 18 | Ser-Pro-Glu-Ala-Gln-Arg-Val-Gln |
| (Ala)10 UAG (6-13)NH$_2$ | 19 | Ser-Pro-Glu-His-Ala-Arg-Val-Gln |
| (Ala)11 UAG (6-13)NH$_2$ | 20 | Ser-Pro-Glu-His-Gln-Ala-Val-Gln |
| (Ala)12 UAG (6-13)NH$_2$ | 21 | Ser-Pro-Glu-His-Gln-Arg-Ala-Gln |
| (Ala)13 UAG (6-13)NH$_2$ | 22 | Ser-Pro-Glu-His-Gln-Arg-Val-Ala |
| (Acetyl-Ser)6 UAG (6-13)NH$_2$ | 23 | Ac-Ser-Pro-Glu-His-Gln-Arg-Val-Gln |
| (Acetyl-Ser)6, (DPro)7 UAG (6-13)NH$_2$ | 24 | Ac-Ser-pro-Glu-His-Gln-Arg-Val-Gln |
| Cyclo (6-13) UAG (also referred to as cyclic UAG (6-13)) | 25 | Ser-Pro-Glu-His-Gln-Arg-Val-Gln (cycl) |
| Cyclo (8, 11), Lys 11, UAG (6-13)amide | 26 | Ser-Pro-Glu-His-Gln-Lys-Val-Gln-amide |
| Cyclo (8, 11), Acetyl-Ser6, Lys 11, UAG (6-13)-amide | 27 | Ac-Ser-Pro-Glu-His-Gln-Lys-Val-Gln (cycl) |
| Acetyl-Ser6, Lys 11, UAG (6-13)NH$_2$ | 28 | Ac-Ser-Pro-Glu-His-Gln-Lys-Val-Gln-NH$_2$ |

Analogs of UAG or analogs of fragments thereof are, for example, analogs obtained by alanine scans, by substitution with D-amino acids or with synthetic amino acids or by cyclization of the peptide. Analogs of UAG or fragments thereof may comprise a non-naturally encoded amino acid, wherein the non-naturally encoding amino acid refers to an amino acid that is not one of the common amino acids or pyrrolysine or selenocysteine, or an amino acid that occur by modification (e.g. post-translational modification) of naturally encoded amino acid (including, but not limited to, the 20 common amino acids or pyrrolysine and selenocysteine) but are not themselves incorporated into a growing polypeptide chain by the translation complex. Examples of such non-naturally-occurring amino acids include, but are not limited to, N-acetylglucosaminyl-L-serine, N-acetylglucosaminyl-L-threonine and O-phosphotyrosine.

As used herein, the term "modified" refers to any changes made to a given polypeptide, such as changes to the length of the polypeptide, the amino acid sequence, chemical structure, co-translational modification, or post-translational modification of a polypeptide.

The term "post-translational modification" refers to any modification of a natural or non-natural amino acid that occurs to such an amino acid after it has been incorporated into a polypeptide chain. The term encompasses, by way of example only, co-translational in vivo modifications, co-translational in vitro modifications (such as in cell-free translation system), post-translational in vivo modifications, and post-translational in vitro modifications. Examples of post-translational modifications are, but are not limited to, glycosylation, acetylation, acylation, amidation, carboxylation, phosphorylation, PEGylation, addition of salts, amides or esters, in particular C-terminal esters, and N-acyl derivatives of the peptides of the invention. The types of post-translational modifications are well known.

Certain peptides according to the present invention may also be in cyclic form, such that the N- or C-termini are linked head-to-tail either directly, or through the insertion of a linker moiety, such moiety itself generally comprises one or more amino acid residues as required to join the backbone in such a manner as to avoid altering the three-dimensional structure of the peptide with respect to the non-cyclic form. Such peptide derivatives may have improved stability and bioavailability relative to the non-cyclized peptides.

Examples of cyclic peptides of the present invention include: cyclic UAG (1-14), cyclic UAG (1-18), cyclic UAG (17-28), cyclic UAG (6-13), cyclic UAG (8-13), cyclic UAG (8-12), cyclic UAG (8-11), cyclic UAG (9-12) and cyclic UAG (9-11) as well as the peptides identified in Table 2.

Methods for cyclizing peptides are well known in the art and for example may be accomplished by disulfide bond formation between two side chain functional groups, amide or ester bond formation between one side chain functional group and the backbone α-amino or carboxyl function, amide or ester bond formation between two side chain functional groups, or amide bond formation between the backbone α-amino and carboxyl functions. These cyclization reactions have been traditionally carried out at high dilution in solution. Cyclization is commonly accomplished while the peptide is attached to the resin. One of the most common ways of synthesizing cyclic peptides on a solid support is by attaching the side chain of an amino acid to the resin. Using appropriate protection strategies, the C- and N-termini can be selectively deprotected and cyclized on the resin after chain assembly. This strategy is widely used, and is compatible with either tert-butyloxycarbonyl (Boc) or 9-fluorenylmethoxycarbonyl (Fmoc) protocols. However, it is restricted to peptides that contain appropriate side chain functionality to attach to the solid support. A number of approaches may be used to achieve efficient synthesis of cyclic peptides. One procedure for synthesizing cyclic peptides is based on cyclization with simultaneous cleavage from the resin. After an appropriate peptide sequence is assembled by solid phase synthesis on the resin or a linear sequence is appended to resin, the deprotected amino group can react with its anchoring active linkage to produce protected cyclic peptides. In general, a final deprotection step is required to yield the target cyclic peptide.

Lactamazation, a form of cyclization, may be performed to form a lactam bridge using Fmoc synthesis, amino acids with different protecting groups at the lateral chains may be introduced, such as, but not limited to, aspartic acid (or glutamic) protected with allyl ester at the beta ester (or gamma ester for glutamic acid) and lysine protected with allyloxy carbamate at the N-ε. At the end of the synthesis, with the N-terminus of the peptide protected with Fmoc, Boc or other protecting group different from Alloc, the allyl and alloc protecting groups of aspartic acid and lysine may be deprotected with, for example, palladium (0) followed by cyclization using PyAOP (7-Azabenzotriazol-1-yloxytris (pyrrolidino) phosphonium-hexafluorophosphate) to produce the lactam bridge.

Unless otherwise indicated, an amino acid named herein refers to the L-form. Well recognized abbreviations in the art will be used to describe amino acids, including levorotary amino acids (L-amino acids or L or L-form) and dextrorotatory amino acids (D-amino acids or D or D-form), Alanine (Ala or A), Arginine (Arg or R), Asparagine (Asn or N), Aspartic acid (Asp or D), Cysteine (Cys or C), Glutamic acid (Glu or E), Glutamine (Gln or Q), Glycine (Gly or G), Histidine (His or H), Isoleucine (Ile or I), Leucine (Leu or L), Lysine (Lys or K), Methionine (Met or M), Phenylalanine (Phe or F), Proline (Pro or P), Serine (Ser or S), Threonine (Thr or T), Tryptophan (Trp or W), Tyrosine (Tyr or Y) and Valine (Val or V). An L-amino acid residue within the native peptide sequence may be altered to any one of the 20 L-amino acids commonly found in proteins or any one of the corresponding D-amino acids, rare amino acids, such as, but not limited to, 4-hydroxyproline or hydroxylysine, or a non-protein amino acid, such as P-alanine or homoserine.

UAG peptides or fragments or analogs thereof may also be part of a fusion protein. It is often advantageous to include an additional amino acid sequence such as a signal sequence which contains for example secretory or leader sequences, pro-sequences, linker sequences which, inter alia, aid in purification such as multiple histidine residues (HA-tag), or an additional sequence for stability during recombinant production. The additional amino acids or sequence may be linked to at the N-terminal or at the C-terminal of the polypeptide or may be linked to any amino acid of the sequences located between the N- and the C-terminal to give rise the UAG peptides or fragment or analogs thereof having a linker moiety.

Any other analogs of UAG or fragments thereof or any other modified UAG or fragments thereof that preserve the biological activity of the full length UAG are encompassed by the present invention.

General methods and synthetic strategies used in providing functional and structural analogs of UAG or fragments thereof are commonly used and well known in the art and are described in publications such as: "Peptide synthesis protocols" ed, M. W. Pennigton & B. M. Dunn. Methods in Molecular Biology. Vol 35. Humana Press, NJ., 1994; "Solid phase peptide synthesis" by Stewart and Young, W. h Freeman & Co., San Francisco, 1969 and Erickson and Merrifield; and "The Proteins" Vol. 2, p. 255 et seq. (Ed. Neurath and Hill), Academic Press, New York, 1976.

As used herein, the term "homology" refers to sequence similarity between two peptides while retaining an equivalent biological activity. Homology can be determined by comparing each position in the aligned sequences. A degree of homology between amino acid sequences is a function of the number of identical or matching amino acids at positions shared by the sequences so that a "homologous sequence" refers to a sequence sharing homology and an equivalent function or biological activity. Assessment of percent homology is known by those of skill in the art.

Methods to determine homology, identity and similarity of peptides are codified in publicly available computer programs. Preferred computer program methods to determine identity and similarity between two sequences include, but are not limited to, the GCG program package, BLASTP, BLASTN, and FASTA. The BLAST X program is publicly available from NCBI and other sources. The well known Smith Waterman algorithm may also be used to determine identity.

Preferred parameters for polypeptide sequence comparison include the following:
Algorithm: Needleman and Wunsch, J. Mol Biol. 48: 443-453 (1970);
Comparison matrix: BLOSSUM62 from Hentikoff and Hentikoff, Proc. Natl. Acad. Sci. USA. 89:10915-10919 (1992);
Gap Penalty: 12; Gap Length Penalty: 4.

A program useful with these parameters is publicly available as the "gap" program from Genetics Computer Group, Madison, Wis. The aforementioned parameters are the default parameters for amino acid sequence comparisons (along with no penalty for end gaps).

The polypeptides of the invention may be prepared in any suitable manner as known in the art. Such polypeptides include isolated naturally occurring polypeptides, recombinantly produced polypeptides, synthetically produced polypeptides, or polypeptides produced by a combination of these methods. Means and methods for preparing such polypeptides are well known in the art.

Certain aspects of the invention use UAG polynucleotides. These include isolated polynucleotides which encode the UAG polypeptides, fragments and analogs defined in the application.

As used herein, the term "polynucleotide" refers to a molecule comprised of a plurality of deoxyribonucleotides or nucleoside subunits. The linkage between the nucleoside subunits can be provided by phosphates, phosphonates, phosphoramidates, phosphorothioates, or the like, or by nonphosphate groups as are known in the art, such as peptoid-type linkages utilized in peptide nucleic acids (PNAs). The linking groups can be chiral or achiral. The oligonucleotides or polynucleotides can range in length from 2 nucleoside subunits to hundreds or thousands of nucleoside subunits. While oligonucleotides are preferably 5 to 100 subunits in length, and more preferably, 5 to 60 subunits in length, the length of polynucleotides can be much greater (e.g., up to 100). The polynucleotide may be any of DNA and RNA. The DNA may be in any form of genomic DNA, a genomic DNA library, cDNA derived from a cell or tissue, and synthetic DNA. Moreover, the present invention may, in certain aspects, use vectors which include bacteriophage, plasmid, cosmid, or phagemid.

The expressions "biological activity" or "biological property", or the term "activity" in reference to the polypeptides of the present invention, are used interchangeably herein and refer to the pharmacological, biological or cellular abilities of the polypeptides of the invention and include, but are not limited to, the capacity of replacing UAG in the biological functions of UAG as described in the present application, such as, but not limited to, modulating AG; inhibiting AG; decreasing circulating AG levels; decreasing circulating elevated AG levels; decreasing circulating AG/UAG ratio; decreasing circulating elevated AG/UAG ratio; ameliorating the symptoms induced by AG levels and/or AG/UAG levels; facilitating, preventing and/or treating conditions associated with circulating AG and/or circulating AG/UAG ratio and facilitating, preventing and/or treating conditions associated with elevated circulating AG and/or elevated circulating AG/UAG ratio.

ii) Therapeutic Methods, Uses and Compositions

According to one embodiment, the modulation of ghrelin levels and/or modulation of AG/UAG ratio in a subject is desirable when such modulation is beneficial to the subject.

According to another embodiment, the present invention provides a method for decreasing AG levels and/or decreasing AG/UAG ratio in a subject. In some implementations of this embodiment, the subject demonstrate elevated AG levels and/or an elevated AG/UAG ratio and the symptoms associated with AG levels and/or associated with AG/UAG ratio are worsen or exacerbated in this subject.

In some implementations of these embodiments, the AG levels refer to the circulating AG levels and the AG/UAG ratio refers to the circulating AG/UAG ratio. In some further implementations of this embodiment, the subject shows one or more of the following symptoms associated with AG levels and/or associated with AG/UAG ratio: hyperglycemia, insulin resistance, reduced fat utilization, adiposity, increase food intake, weight gain and suppression of insulin secretion. In further implementations of this embodiment, the subject suffers from one or more of the following conditions associated with the symptoms defined above: diabetes (e.g., type 2 diabetes), Prader-Willi Syndrome (PWS), obesity, obesity associated with insulin resistance, hyperphagia and hyperghrelinemia. The method comprises administering an effective amount of UAG, fragments, analogs, pharmaceutical salts thereof, and/or any combinations thereof to the subject.

According to another embodiment, the present invention provides a method for ameliorating and/or diminishing the symptoms associated with AG levels and/or associated with AG/UAG ratio in a subject. In some implementations of this embodiment, the subject demonstrate elevated AG levels and/or an elevated AG/UAG ratio and the symptoms associated with AG levels and/or associated with the AG/UAG ratio are worsen or exacerbated in this subject. The present invention thus also provides a method for ameliorating and/or diminishing the symptoms associated with elevated AG levels and/or associated with elevated AG/UAG ratio in such subject.

The symptoms associated with elevated AG levels include, but are not limited to, hyperglycemia, insulin resistance, reduced fat utilization, adiposity, increased food intake, weight gain and suppression of insulin secretion. The symptoms associated with elevated AG/UAG ratio include, but are not limited to, insulin resistance. In some implementations of theses embodiment, the subject suffers from one or more of the following conditions associated with the symptoms defined above: diabetes (e.g. type 2 diabetes), Prader-Willi Syndrome (PWS), obesity, obesity associated with insulin resistance, hyperphagia and hyperghrelinemia. The method comprises administering an effective amount of UAG, fragments, analogs, pharmaceutical salts thereof, and/ or any combinations thereof to the subject. In some further implementations of this embodiment, the AG levels refer to the circulating AG levels and the AG/UAG ratio refers to the circulating AG/UAG ratio. The method comprises administering an effective amount of UAG, fragments, analogs, pharmaceutical salts thereof and/or any combinations thereof to the subject.

According to yet another embodiment, the present invention provides for a method of ameliorating and/or treating a condition, a disorder or a disease associated with AG levels and/or associated with AG/UAG ratio. In some implementations of this embodiment, the AG levels refer to the circulating AG levels and the AG/UAG ratio refers to the circulating AG/UAG ratio. Conditions, disorders or diseases associated with AG levels include, but are not limited to, diabetes (e.g., type 2 diabetes), Prader-Willi Syndrome (PWS), obesity, obesity associated with insulin resistance, hyperphagia and hyperghrelinemia. The method comprises administering an effective amount of UAG, fragments, analogs, pharmaceutical salts thereof and/or any combination thereof to the subject.

As used herein, the term "hyperghrelinemia" refers to a pathological condition caused by elevated circulating AG levels and/or by an elevated circulating AG/UAG ratio. Subjects suffering from hyperghrelinemia exhibit symptoms such as, but not limited to, hyperglycemia, insulin resistance, decreased insulin secretion, decreased fat utilization, adiposity, weight gain and/or a combination thereof.

In some implementations of the present invention, the more the AG levels are elevated in these subjects, the more pronounced are the symptoms induced by elevated AG levels and the more efficient is UAG, fragments, analogs and/or pharmaceutical salts thereof in ameliorating and/or diminishing these symptoms.

In some other implementations of the present invention, the more the AG/UAG ratio is elevated in these subjects, the more pronounced are the symptoms induced by an elevated AG/UAG ratio and the more efficient is UAG, fragments, analogs and/or pharmaceutical salts thereof in ameliorating and/or diminishing these symptoms.

According to yet another embodiment, the present invention provides for a method for counteracting the peripheral actions of AG as well as to decrease AG levels and to ameliorate the symptoms induced by AG levels.

To the extent that new and yet uncovered conditions, diseases and disorders can be ameliorated, prevented and/or treated with the reduction in AG and/or a reduction in AG/UAG ratio, the methods of the present invention can be utilized with respect to those conditions, disorders and diseases.

In one implementation of these embodiments, the method includes the step of administering an effective amount of UAG or of a polypeptide defined herein which shares the same potential therapeutic indication as UAG itself to the subject in need of such administration. Such polypeptide comprises the amino acid sequence set forth in SEQ ID NO: 1, or comprises any fragment or any analog thereof such as for example, those described in the above tables.

The actions of UAG have previously been shown to be conserved by fragments UAG (6-13) (SEQ ID NO: 6), UAG (8-13) (SEQ ID NO: 7), UAG (8-12) (SEQ ID NO: 8), UAG (8-11) (SEQ ID NO: 12), UAG (9-12) (SEQ ID NO: 11) and UAG (9-11) (SEQ ID NO: 29). U.S. Pat. Nos. 8,222,217 and 8,318,664, incorporated herein in their entirety, have shown that these fragments retain the activity of UAG full length on glucose, insulin and lipid metabolisms. A peptide with the inverse sequence of UAG (1-14) (SEQ ID NO: 3) and named UAG (14-1) (SEQ ID NO: 30) was used as a negative control in the experiments testing UAG fragments. UAG (8-11) (SEQ ID NO: 10) was shown to be the smallest UAG fragment to retain UAG activities. The results provided herein further indicate that UAG fragments, such as for example, UAG (6-13) (SEQ ID NO: 6) and cyclic UAG (6-13) (SEQ ID NO: 25) retain UAG's ability to decrease AG levels and decrease AG/UAG ratio.

In a further embodiment, UAG, fragments and/or analogs thereof are used to reduce the elevated AG levels associated with Prader-Willi Syndrome (PWS). People who suffer from PWS suffer from slowed development, severe obesity and an insatiable appetite. Their hunger is so strong that it often requires custodial enforcement of food availability to avert early death as a result of hyperphagia. AG concentrations in these subjects are higher than normal. This correlation between hyperphagia and increase AG levels is consistent with the known orexigenic effect of AG. The data present herein demonstrate that administration of UAG can decrease the elevated AG levels in PWS subjects. The methods of the invention can be used to help patients with Prader-Willi syndrome reduce their ghrelin levels to more normal/healthier levels, curb their appetite, and/or ameliorate other manifestations of this disorder. This decrease in AG is expected to translate into a decrease in appetite and in a subsequent reduction in fat mass associated with PWS.

As used herein, the term "hyperphagia" refers to excessive hunger and abnormally large intake of solids by mouth. Hyperphagic conditions may occur in association with for example, central nervous system (CNS) disorders including gangliocytoma of the third ventricle, hypothalmic astrocytoma, Kleine-Levin Syndrome, Froehlich's Syndrome, Parkinson's Disease, genetic disorders including Praeder-Willi Syndrome, major psychiatric disorders including anxiety, major depressive disorder, depressive phase of bipolar disorder, seasonal affective disorder, and schizophrenia, psychotropic medication, including delta-9 tetrahydrocannabinol, antidepressants and neuroleptics and sleep disorders including sleep apnea. Hyperphagia may occur in psychiatric disorders such as depression, anxiety and schizophrenia. In some embodiments, administration of UAG, fragments and/or analogs thereof may reduces the hyperphagia associated with these conditions.

As used herein, the term "treatment" refers to both therapeutic treatments as well as to prophylactic measures. Those in need of treatment include those already with the disorder, disease or condition as well as those in which the disease, disorder or condition is to be prevented. Those in need of treatment are also those in which the disorder, disease or condition has occurred and left after-effects or scars. Treatment also refers to administering a therapeutic substance effective to improve or ameliorate, diminish symptoms associated with a disease, a disorder or a condition to lessen the severity of or cure the disease, disorder or condition, or to prevent the disease, disorder or condition from occurring or reoccurring.

Studies have demonstrated a persistent increase in plasma AG levels up to one year following a diet-induced weight loss in obese subjects (Refs. 28 and 29). The reduction of elevated AG levels in these subjects could thus prevent obesity relapse while the subject is under diet. Therefore, in yet a further embodiment, the present invention provides a method for improving the efficacy of diet-induced weight loss and/or for preventing weight gain following diet-induced weight loss in a subject in need of weight loss or in need of maintaining a weight loss by administering an effective amount of UAG, fragments, analogs and/or pharmaceutical salts thereof to the subject.

In a further implementation of this embodiment, UAG, fragments and/or analogs thereof are administered at the onset of the diet program and preferably, UAG, fragments and/or analogs thereof are also administered throughout the diet program.

It is a further aspect of the present invention to provide for any pharmaceutical composition incorporating at least one of the polypeptides as defined herein.

For therapeutic and/or pharmaceutical uses, the polypeptides as defined herein may be formulated for, but not limited to, intravenous, subcutaneous, transdermal, topical, oral, buccal, sublingual, nasal, inhalation, pulmonary, or parenteral administration according to conventional methods. Intravenous injection may be by bolus or infusion over a conventional period of time. The polypeptides as defined herein may also be administered directly to a target site within a subject e.g., by biolistic delivery to an internal or external target site or by catheter to a site in an artery.

In one embodiment, the polypeptides defined herein are administered as a bolus. Accordingly, in one implementation of this embodiment, the medicament is administered as a bolus prior to meal, wherein the bolus comprises an effective amount of UAG, a fragment and/or an analog thereof of a salt thereof. The bolus may be administered one, twice, three times or more daily or may be administered according to other dosage regimens.

Suitable dosage regiments are determined taking into account factors well known in the art such as, but not limited to, type of subject being dosed, the age, the weight, the sex and the medical condition of the subject, the route of administration, the desired affect, etc.

Active ingredients, such as the polypeptides defined herein, may be administered orally as a suspension and can be prepared according to techniques well known in the art of pharmaceutical formulation and may contain, but not be limited to, microcrystalline cellulose for imparting bulk, alginic acid or sodium alginate as a suspending agent, methylcellulose as a viscosity enhancer, and sweeteners/flavoring agents. As immediate release tablets, these compositions may contain, but are not limited to microcrystalline cellulose, dicalcium phosphate, starch, magnesium stearate and lactose and/or other excipients, binders, extenders, disintegrants, diluents and lubricants. The active ingredients may be administered by way of a controlled-release delivery system.

Administered by nasal aerosol or inhalation formulations may be prepared, for example, as solutions in saline, employing benzyl alcohol or other suitable preservatives, absorption promoters to enhance bioavailability, employing fluorocarbons, and/or employing other solubilizing or dispersing agents.

The polypeptides of the invention may be administered in intravenous (both bolus and infusion), intraperitoneal, subcutaneous, topical with or without occlusion, or intramuscular form. When administered by injection, the injectable solution or suspension may be formulated using suitable non-toxic, parenteral-acceptable diluents or solvents, well known in the art.

The polypeptides of the invention may also be formulated for topical administration. The term "topical" as used herein includes any route of administration that enables the compounds to line the skin or mucosal tissues.

The formulation suitable for topical application may be in the form of, for example, cream, lotion, solution, gel, ointment, paste, plaster, paint, bioadhesive, or the like, and/or may be prepared so as to contain liposomes, micelles, microparticles and/or microspheres. The formulation may be aqueous, i.e., contain water, or may be non-aqueous and optionally used in combination with an occlusive overlayer so that moisture evaporating from the body surface is maintained within the formulation upon application to the body surface and thereafter.

Ointments, as is well known in the art of pharmaceutical formulation, are semisolid preparations that are typically based on petrolatum or other petroleum derivatives.

Formulations may also be prepared with liposomes, micelles, microparticles and/or microspheres. Liposomes are microscopic vesicles having a lipid wall comprising a lipid bilayer, and can be used as drug delivery systems. Micelles are known in the art to be comprised of surfactant molecules arranged so that their polar head groups form an outer spherical shell, while the hydrophobic, hydrocarbon chains are oriented towards the center of the sphere, forming a core. Microparticles are particulate carrier systems in the micron size range, normally prepared with polymers, which can be used as delivery systems for drugs or vaccines that are usually trapped within the particles. Microspheres, similarly, may be incorporated into the present formulations and drug delivery systems. Like liposomes and micelles, microspheres essentially encapsulate a drug or drug-containing formulation. Microspheres are generally, although not necessarily, formed from synthetic or naturally occurring biocompatible polymers, but may also be comprised of charged lipids such as phospholipids.

Preparations of formulations suitable for topical administration are well known in the art and described in the pertinent texts and literature.

In general, pharmaceutical compositions will comprise at least one of the polypeptides of the invention together with a pharmaceutically acceptable carrier which will be well known to those skilled in the art. The compositions may further comprise for example, one or more suitable excipients, diluents, fillers, solubilizers, preservatives, carriers, salts, buffering agents and other materials well known in the art depending upon the dosage form utilized. Methods of composition are well known in the art.

In the present context, the term "pharmaceutically acceptable carrier" is intended to denote any material, which is inert in the sense that it substantially does not have any therapeutic and/or prophylactic effect per se and that is non-toxic. A pharmaceutically acceptable carrier may be added to the polypeptides of the invention with the purpose of making it possible to obtain a pharmaceutical composition, which has acceptable technical properties.

Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG.

Carriers for topical or gel-based forms of polypeptides include polysaccharides such as sodium carboxymethylcellulose or methylcellulose, polyvinylpyrrolidone, polyacrylates, polyoxyethylene-polyoxypropylene-block polymers, PEG, and wood wax alcohols.

The polypeptides used for in vivo administration must be sterile. This may be accomplished by filtration through sterile filtration membranes, prior to or following lyophilization and reconstitution. The polypeptides ordinarily will be stored in lyophilized form or in solution. Therapeutic polypeptide compositions generally are placed into a container having a sterile access port, for example, an intravenous solution bag or vial having a stopper pierceable by a hypodermic injection needle.

For use in the methods defined herein, the invention also provides an article of manufacture or a commercial package or kit, comprising: a container, a label on the container, and a composition comprising the polypeptides of the invention as an active agent within the container when used at the indicated level, wherein the composition is effective for, inter alia, modulating AG; inhibiting AG; decreasing circulating AG levels; decreasing circulating elevated AG levels; decreasing circulating AG/UAG ratio; decreasing circulating elevated AG/UAG ratio; ameliorating the symptoms induced by AG levels and/or AG/UAG levels; facilitating, preventing and/or treating conditions associated with circulating AG and/or circulating AG/UAG ratio and/or facilitating, preventing and/or treating conditions associated with elevated circulating AG and/or elevated circulating AG/UAG ratio.

An "effective amount" or a "therapeutically effective amount" refers to an amount effective, at dosages and for periods of time necessary, to achieve the desired therapeutic result. A therapeutically effective amount of the peptides noted herein may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as to modulate AG; inhibit AG; decrease circulating AG levels; decrease circulating elevated AG levels; decrease circulating AG/UAG ratio; decrease circulating elevated AG/UAG ratio; ameliorate the symptoms induced by AG levels and/or AG/UAG levels; facilitate, prevent and/or treat conditions associated with circulating AG and/or circulating AG/UAG ratio and/or facilitate, prevent and/or treat conditions associated with elevated circulating AG and/or elevated circulating AG/UAG ratio. A prophylactically effective amount can be determined as described above for the therapeutically effective amount. For any particular subject, specific dosage regimens may be adjusted over time according to the individual need and the professional judgment of the person administering or supervising the administration of the compositions.

For example, a therapeutically effective amount or effective dose of the peptides of the invention (also referred to herein as "active compound") is an amount sufficient to modulate AG; inhibit AG; decrease circulating AG levels; decrease circulating elevated AG levels; decrease circulating AG/UAG ratio; decrease circulating elevated AG/UAG ratio; ameliorate the symptoms induced by AG levels and/or AG/UAG levels; facilitate, prevent and/or treat conditions associated with circulating AG and/or circulating AG/UAG ratio and/or facilitate, prevent and/or treat conditions associated with elevated circulating AG and/or elevated circulating AG/UAG ratio. The methods and/or assays for measuring such parameters are known to those of ordinary skill in the art.

The therapeutically effective amount of the invention will generally vary from about 0.001 µg/kg to about 10 mg/kg, more particularly from about 0.01 µg/kg to about 10 mg/kg, and even more particularly from about 1 µg/kg to about 1 mg/kg. Therapeutically effective amounts or effective doses that are outside this range but that have the desired therapeutic effect are also encompassed by the present invention.

In a one embodiment, the subject noted above is a mammal, in a further aspect, a human.

In a further embodiment, the present polypeptides may be administered in combination with additional pharmacologically active substances or may be administered in combination with another therapeutic method. The combination may be in the form of a kit-in-part system, wherein the combined active substances may be used for simultaneous, sequential or separate administration.

iii) AG Levels and AG/UAG Ratio as Biomarkers

According to another embodiment, the present invention relates to the use of circulating AG levels and the use of circulating AG/UAG ratio as biomarkers for the identification of subjects that are likely to respond to and/or benefit from a treatment comprising the administration of a therapeutically effective amount of UAG, a fragment thereof and/or an analog thereof.

In one implementation of this embodiment, circulating AG levels and/or circulating AG/UAG ratio are measured in a blood sample obtained from a subject according to known methods in the art. The level of circulating AG and/or the ratio of circulating AG/UAG are then processed in part based on reference circulating levels of AG and reference circulating AG/UAG ratios (derived, for example, from the subject himself or from a population of control subjects) so as to derive information which conveys whether the subject has an abnormal level of circulating AG (i.e., below or above a normal or healthy level) and/or an abnormal ratio of circulating AG/UAG (i.e., below or above a normal or healthy ratio). An information which conveys that the subject has an elevated circulating AG level and/or an elevated circulating AG/UAG ratio indicates that the subject is likely to respond to administration of UAG, a fragment thereof or an analog thereof. Administration of UAG, a fragment thereof or an analog thereof in such subject is thus likely to decrease circulating AG levels and/or circulating AG/UAG ratio as well as to lessen the effects associated with elevated circulating AG levels and elevated circulating AG/UAG ratio.

In another implementation of this embodiment, the subject suffers from a condition such as, but not limited to, diabetes (type 1 or type 2), obesity, Prader-Willy, insulin resistance, hyperphagia and hyperghrelinemia. The biomarkers defined herein may be used to determine if such subject is likely to response and/or is likely to benefit from administration of UAG, a fragment thereof or an analog thereof. A subject suffering from such a condition and having an elevated circulating AG level and/or an elevated circulating AG/UAG ratio is likely to respond and/or benefit from administration of UAG, a fragment thereof and/or an analog thereof.

In another implementation of this embodiment, the biomarkers may be used for identifying subjects within a population of subjects that are likely to respond to and/or benefit from administration of a therapeutically effective amount of UAG, a fragment thereof or an analog thereof. In this implementation, the subjects of the population suffer from a condition such as, but not limited to, diabetes (type I or type 2), Prader-Willi Syndrome (PWS), obesity, insulin resistance, hyperphagia and hyperghrelinemia.

In accordance with another implementation of this embodiment, the present invention provides a method of displaying information conveying a subject's likelihood of responding to and/or benefiting from administration of UAG, a fragment thereof and/or an analog thereof. Such implementation may, for example, by carried out by an apparatus, such as, but not limited to, a computer readable storage medium storing a program element suitable for execution by a computer unit. In such implementation, the program element implements a graphical user interface module which displays information conveying the subject's likelihood of responding to and/or benefiting from administration of UAG, a fragment thereof and/or an analog thereof.

The graphical user interface module is adapted for displaying a set of user modifiable information fields allowing a user to enter a set of information data elements associated to the subject's level of circulating AG, level of circulating UAG and/or circulating AG/UAG ratio measured according to methods known in the art. The graphical user interface module is also adapted for displaying a control allowing a user to cause the set of information data elements to be transmitted to a processing unit. The processing unit is adapted to derive a subject's likelihood of responding to and/or benefiting from administration of UAG, a fragment thereof and/or an analog thereof at least in part on the basis of the set of information data elements. The graphical user interface module receives the subject's level of circulating AG, level of circulating UAG and/or circulating AG/UAG ratio and is adapted to display the subject's likelihood of responding to and/or benefiting from administration of UAG, a fragment thereof and/or an analog thereof with reference to normal or healthy circulating AG levels and/or normal or healthy circulating AG/UAG ratio (derived, for example, from the subject or from a population of control subjects). Optionally, the graphical user interface module is adapted to display the subject's likelihood of responding to and/or benefiting from administration of UAG, a fragment thereof and/or an analog thereof with reference to circulating AG levels and/or circulating AG/UAG ratio observed in subjects suffering from a condition such as, but not limited to, diabetes (type I or type 2), Prader-Willi Syndrome (PWS), obesity, insulin resistance, hyperphagia and hyperghrelinemia In accordance with a specific implementation, the set of information data elements may also comprise a gender component, a weight component, a body mass index (BMI) component, a fitness component. The set of information data elements may further include any other suitable item of information associated with the subject.

In accordance with a specific implementation, the subject's likelihood of responding to and/or benefiting from administration of UAG, a fragment thereof and/or an analog thereof includes an indicative data element conveying a likelihood of responding to and/or benefiting from administration of UAG, a fragment thereof and/or an analog thereof. The indicative data element may be expressed in the form of a score, likelihood, a percentile value or in any other format suitable.

In accordance with a specific implementation, the graphical user interface module is adapted for displaying a graph conveying the likelihood of a subject to respond to and/or to benefit from administration of AUG, a fragment thereof and/or an analog thereof, the graph conveying: a first information indicative of a reference normal/healthy level of circulating AG and/or a reference normal/healthy circulating AG/UAG ratio (optionally, the graphical user interface module is adapted for displaying information indicative of reference circulating AG levels and circulating AG/UAG ratios in subjects suffering from a condition such as, but not limited to, diabetes (type I or type 2), Prader-Willi Syndrome (PWS), obesity, insulin resistance, hyperphagia and hyperghrelinemia); a second information indicative of the subject's circulating level of AG, circulating level of UAG and/or circulating AG/UAG ratio; and a third information conveying a likelihood of the subject to respond to and/or to benefit from UAG administration Experiments and Data Analysis The data present herein reports a strong suppressing effect of UAG on serum AG levels and on serum AG/UAG ratio in T2DM subjects.

A continuous overnight (15 hours) infusion of two doses of UAG (3 μg UAG/kg/hr and 10 μg UAG/kg/hr) versus placebo in a cross-over model on the AG concentrations was performed in eight overweight subjects with type 2 diabetes. FIG. 1 depicts a schematic representation of the study protocol. Glucose and insulin responses to a standard breakfast meal (SBM) in the subjects and reasonable metabolic control were assessed. During the infusions with UAG, subjects did not report more side effects than placebo. Laboratory evaluations showed no significant changes in chemistry or parameters and the side effects were not dose-dependent.

Infusion of UAG Decreases Plasma AG Levels

Figures 2A, 2B:
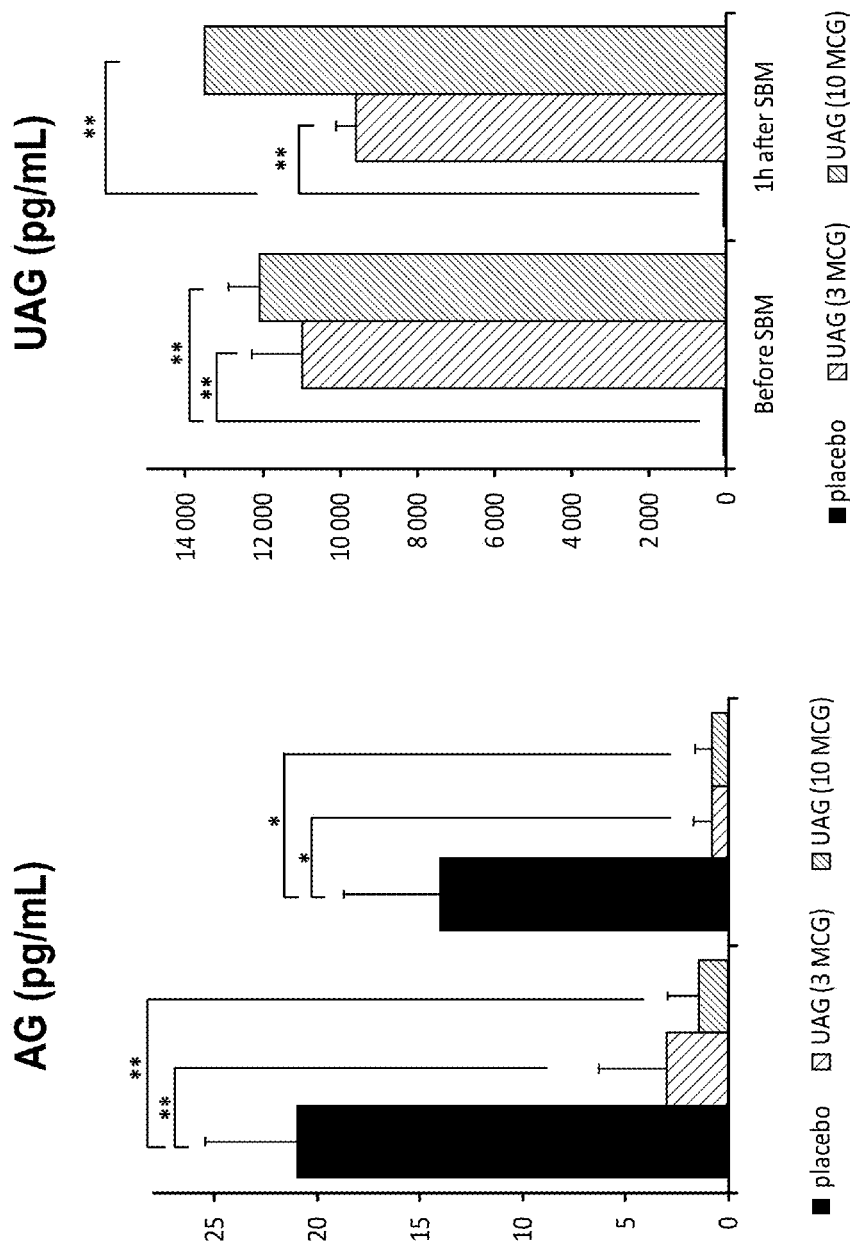
FIGS. 2A and 2B are graphs illustrating the effect of UAG infusion on AG serum levels in T2DM subjects.

The data present in FIGS. 2A and 2B show the changes in serum AG levels (FIG. 2A) and UAG levels (FIG. 2B) before and after SBM. Before initiation of SBM, AG levels are significantly decreased from 21.01±8.9 pg/ml (mean±SD) during placebo infusion to 3.0±6.7 pg/ml in the presence 3 mcg/kg·hr UAG infusion and to 1.4±3.2 pg/ml in the presence of 10 mcg/kg·hr UAG infusion. AG levels are also decreased following SMB from 14.03±9.4 pg/ml in placebo to 0.8±1.8 pg/ml in the presence 3 mcg/kg·hr UAG infusion and to 0.8±1.8 pg/ml in the presence of 10 mcg/kg·hr UAG infusion (FIG. 2A). In parallel, an overnight infusion of UAG resulted in an increase in UAG levels (FIG. 2B). UAG levels increased from 105.9±31.4 (mean±SD) pg/ml in placebo infusion and before start of the SBM to 10998±2623 pg/ml in the presence 3 mcg/kg·hr UAG infusion and to 12085±1616 pg/ml in the presence of 10 mcg/kg·hr UAG infusion. These results indicate that administration of UAG reduces serum AG levels in T2DM subjects.

Infusion of UAG Fragment Counteracts AG-Induced Food Intake

Figure 8:
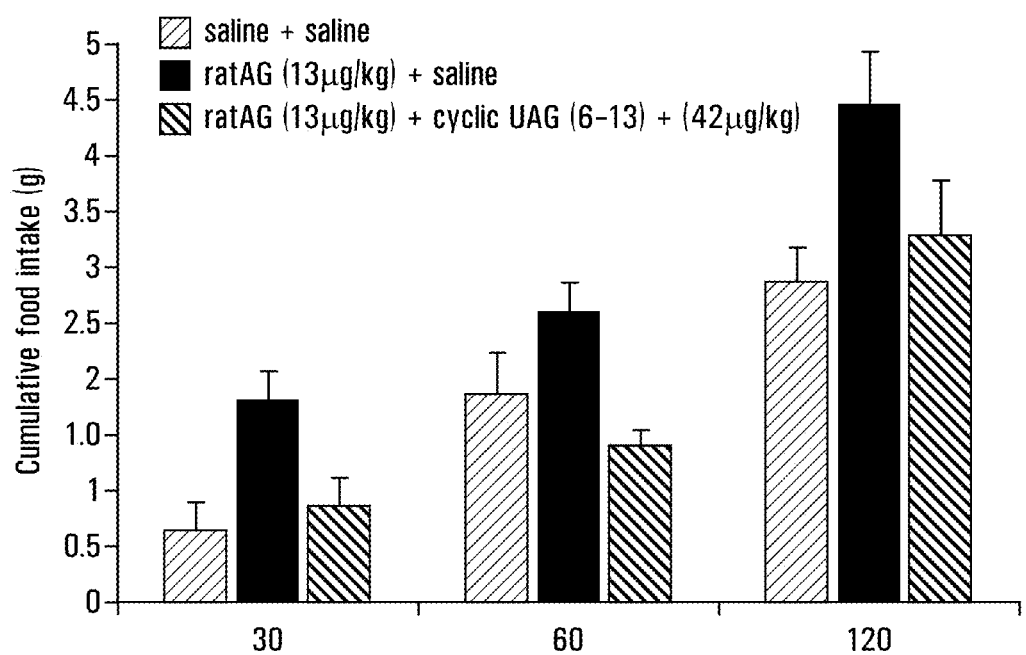
FIG. 8 is a graph illustrating the effects of cyclic UAG fragment (6-13) on AG-induced food intake over the indicated study period. *p<0.001: Kruskal-Wallis One Way ANOVA. Differences between groups were evaluated by the Dunn's test.

A cyclized fragment of UAG, namely cyclic UAG (6-13) as depicted in SEQ ID NO: 25, was able to counteract the orexigenic effects induced by AG in rat (FIG. 8). These results demonstrate that UAG fragments as defined herein which retain the core sequence responsible for UAG-related actions/activities also retain their effects on AG levels. As discussed above, there is a benefit of inhibiting the effect of AG or its levels (e.g. decreasing food consumption) in certain subjects. These results demonstrate a beneficial role for UAG in the treatment of patients with Prader Willi syndrome, in whom elevated AG levels are associated with hyperphagia. Inhibition of AG levels and/or biological effects should thus result in decreased appetite and/or food consumption.

Infusion of UAG Decreases Post-Prandial Plasma Glucose Levels

Figures 3A, 3B:
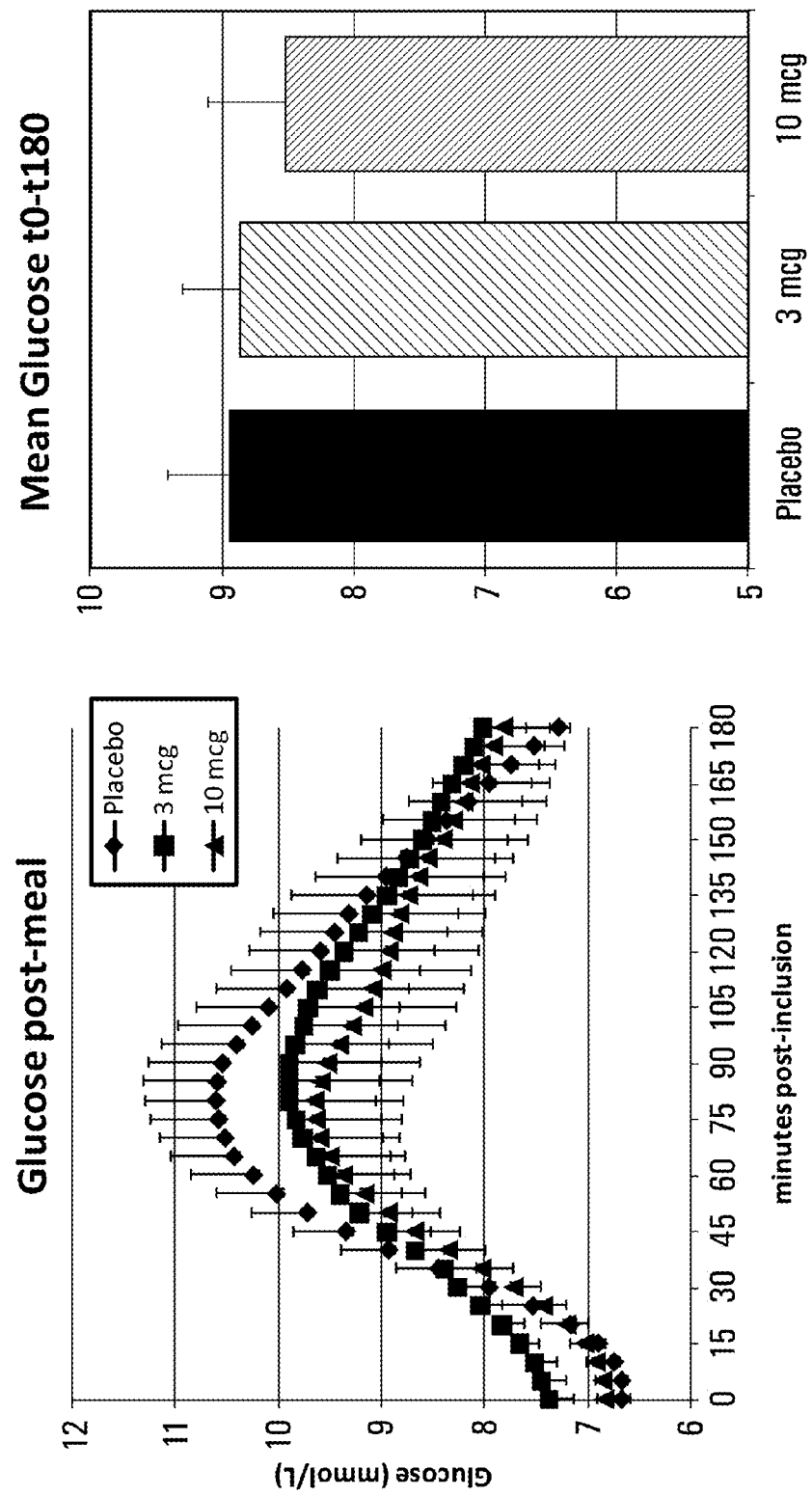
FIGS. 3A and 3B are graphs illustrating the mean post-prandial glucose levels in T2DM subjects as measured with a continuous glucose monitoring device (CGMS® iPro™ Continuous Glucose Recorder, Medtronic trading, The Netherlands).
Figures 4A, 4B:
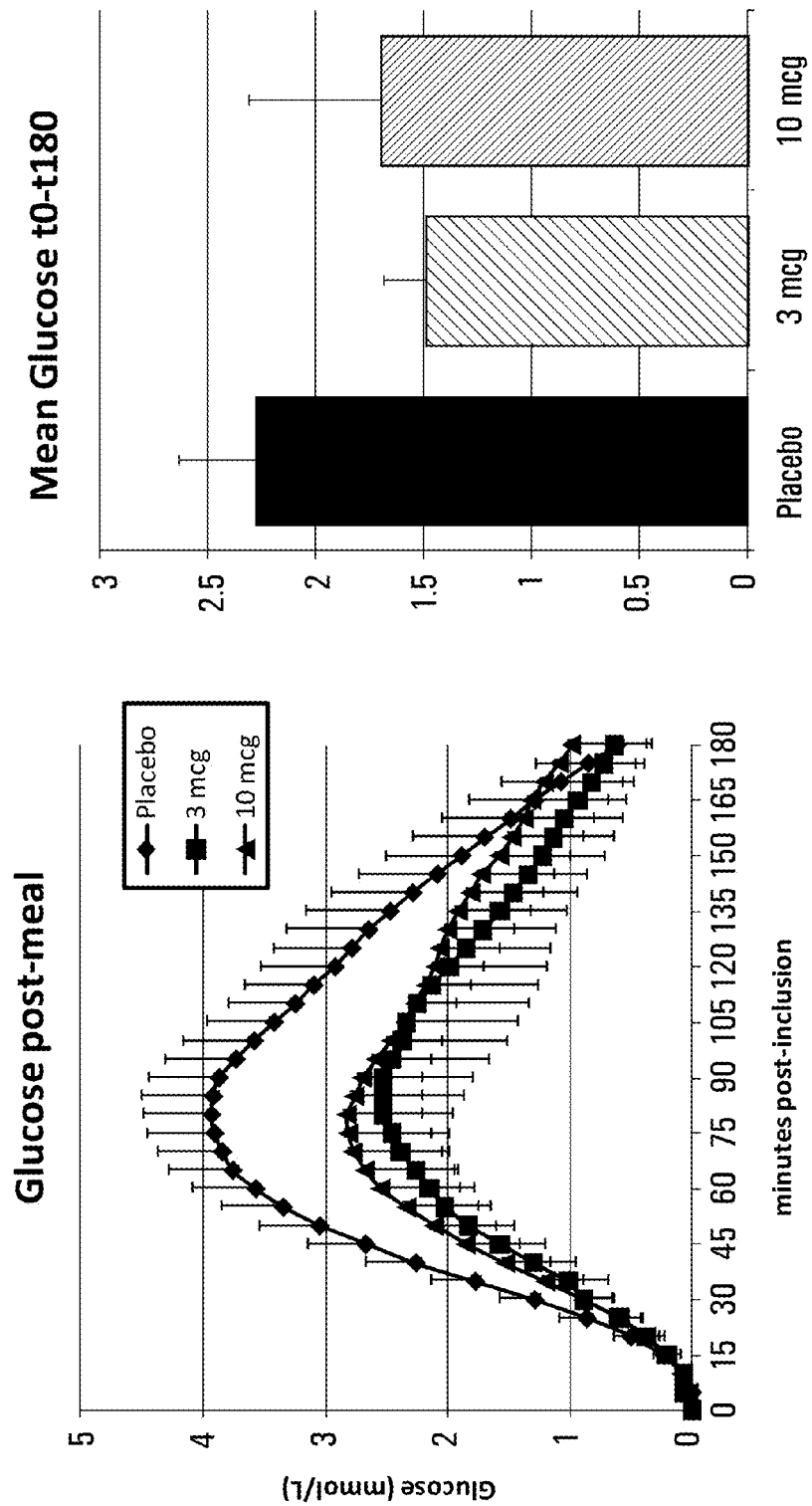
FIGS. 4A and 4B are graphs illustrating the mean postprandial glucose levels in T2DM subjects.
Figures 5A, 5B:
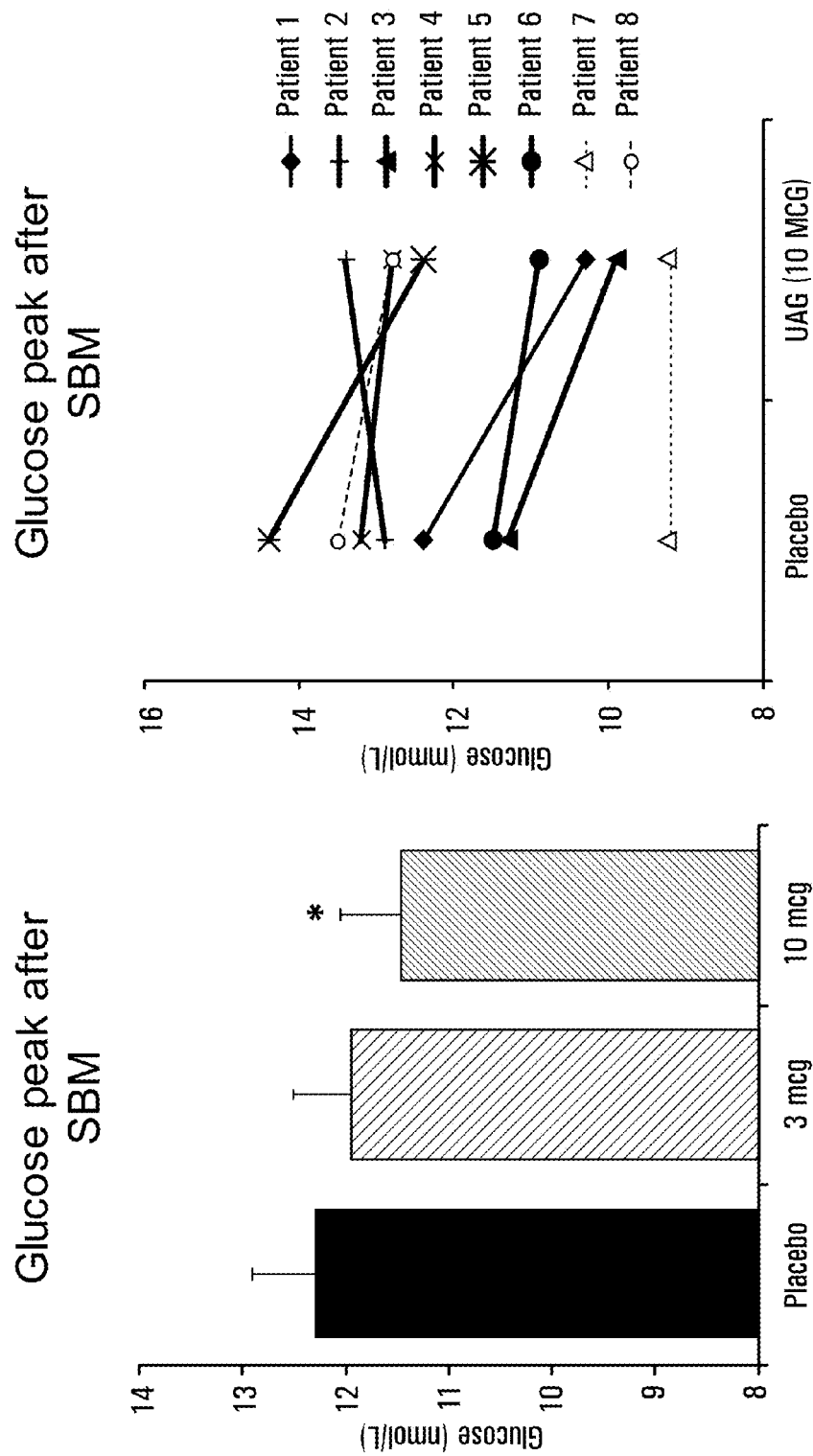
FIGS. 5A and 5B are graphs illustrating the peak plasma glucose levels after SBM in the eight subjects of the study following placebo, UAG 3 mcg/kg/h and UAG 10 mcg/kg/h infusions. Wilcoxon matched-pairs signed rank test; *: 10 mcg vs. Placebo, p<0.05.

An overnight infusion of UAG significantly depressed post-prandial glucose levels as assessed by iPro continuous glucose monitoring (FIGS. 3A and 3B). The area under the curves decreased from 1618 mmol/3 hrs for placebo infusion to 1601 mmol/3 hrs and 1540 mmol/3 hrs for the 3 and 10 mcg UAG infusions respectively. FIGS. 4A and 4B depict the results obtained as changes from the glucose pre-SBM baseline. The area under the curves decreased for the 3 and 10 mcg UAG infusions doses when compared to placebo. FIGS. 5A and 5B indicate a decrease in plasma glucose peak after SBM when UAG is administered. An overall decrease in post-prandial plasma glucose peaks can be observed in the subjects (FIG. 5B). Overall, these data indicate that administration of UAG decreases post-prandial plasma glucose levels in subjects with T2DM.

Figure 6A:
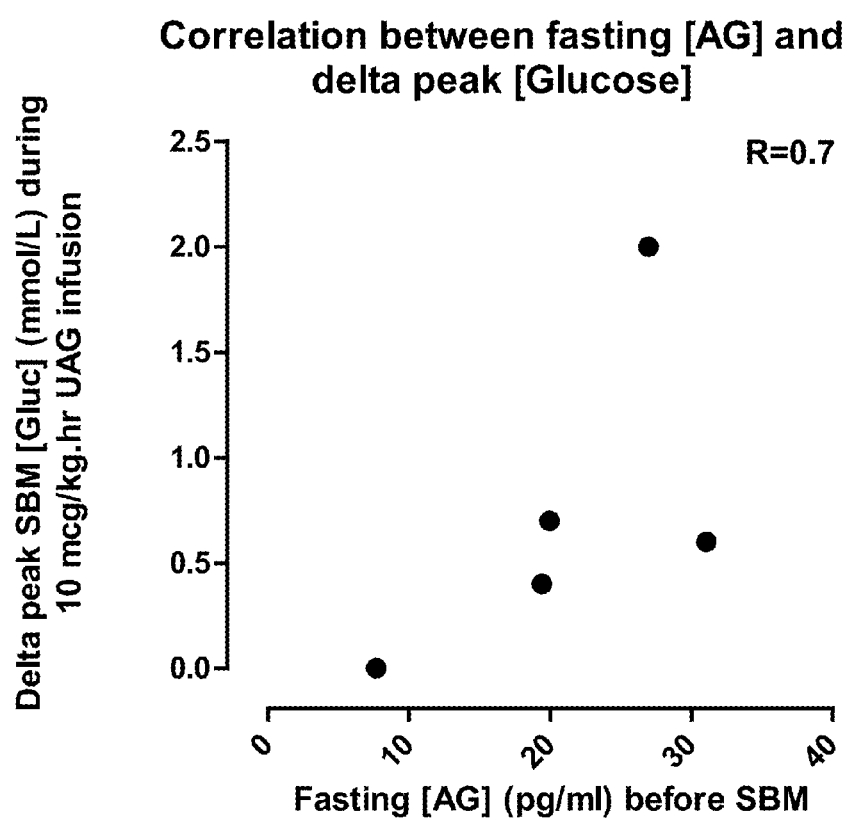
FIGS. 6A, 6B and 6C are graphs indicating the existence of a correlation between fasting basal AG and/or UAG concentrations and glycemic response to UAG administration. The graph in FIG. 6A illustrates the correlation between fasting basal AG levels and change (following UAG vs. placebo administration) in peak glucose levels after SBM. The graph in FIG. 6B illustrates the correlation between fasting basal AG levels and change (following UAG vs. placebo administration) in AUC glucose levels after SBM using iPro continuous glucose measurements. The graph in FIG. 6C illustrates the correlation between the ratio of fasting basal AG over UAG levels and change (following UAG vs. placebo administration) in AUC glucose levels after SBM using iPro continuous glucose measurements.
Figure 6B:
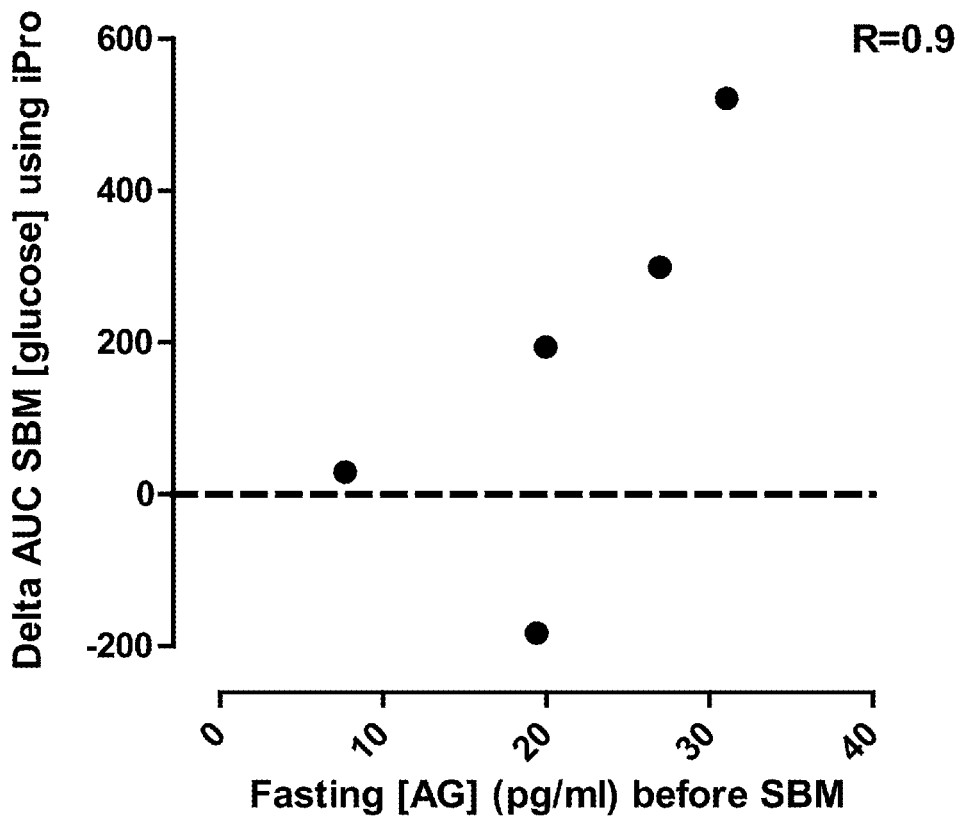
Figure 6C:
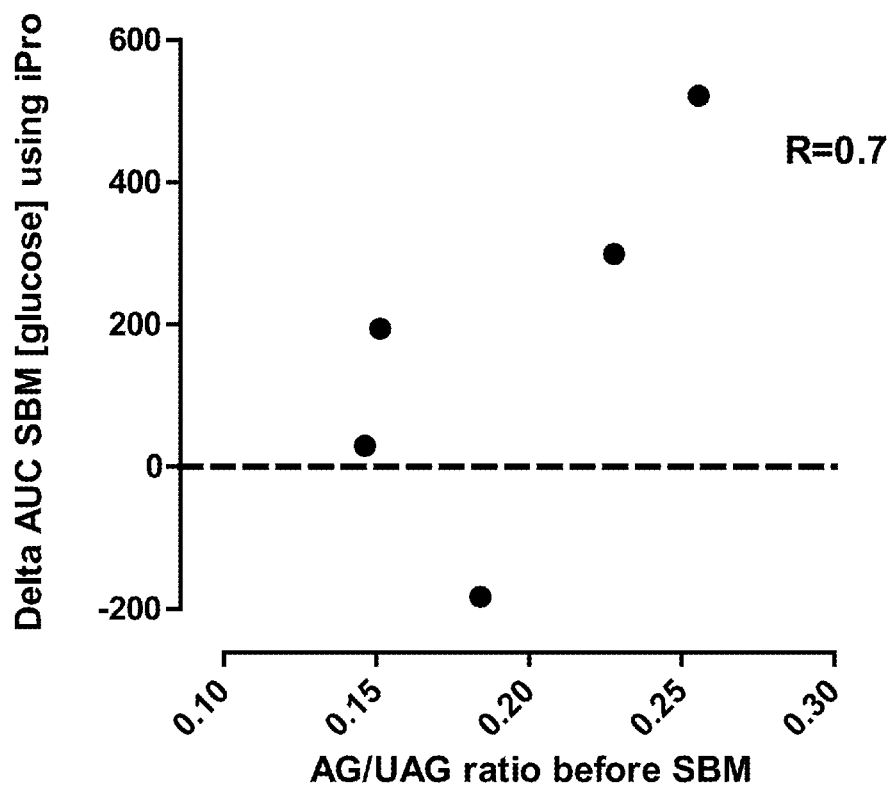

UAG-Induced Reduction in Plasma AG Levels and AG/UAG Ratio Correlates with Reduction in Glucose Levels The inventors were able to show the existence of a correlation between fasting AG levels and/or UAG levels and glycemic response following UAG administration using a standard glucokinase assay. Further to demonstrating such correlation, FIG. 6A shows that the more elevated the fasting AG levels are, the best are the hypoglycemic effect of UAG administration. FIG. 6B also shows the same correlation and effect using iPro continuous glucose measurements. Fasting AG/UAG ratio also correlates with the glycemic response following UAG administration (FIG. 6C). The higher AG/AUG ratios correlate with the best hypoglycemic effect of UAG infusion using iPro continuous glucose measurements.

Infusion of UAG Improves Insulin Sensitivity

Figure 7A:
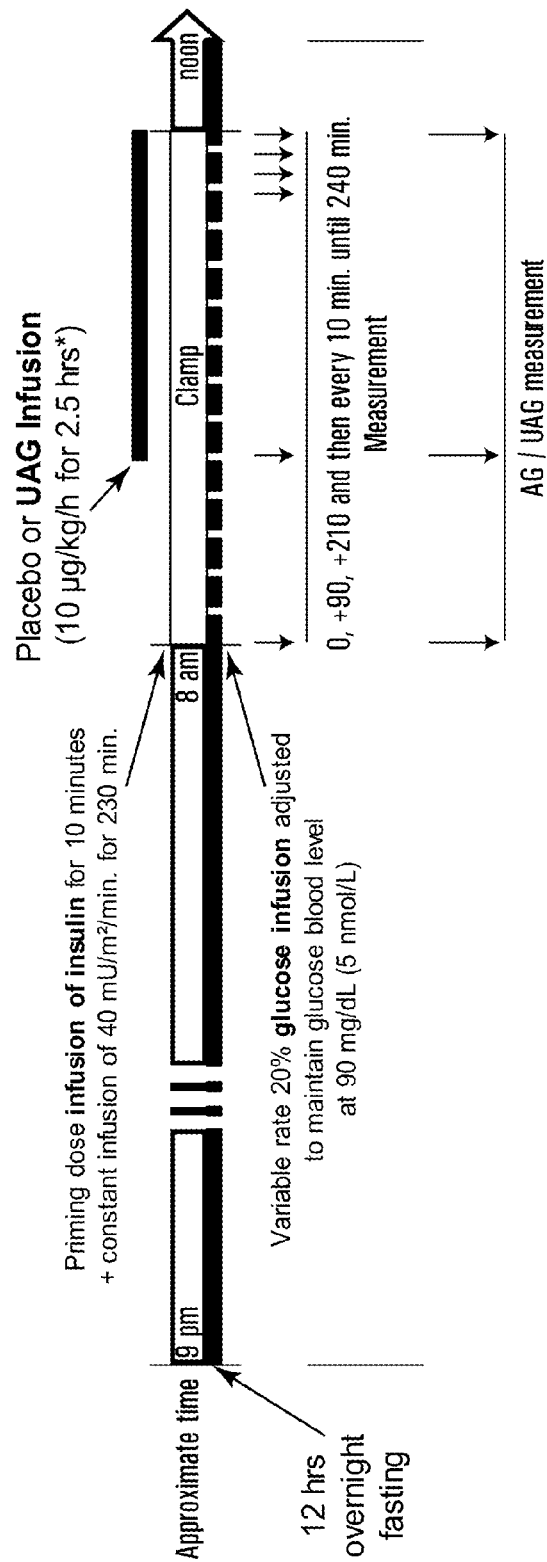
FIG. 7A is a schematic representation of a Hyperinsulinemic-Euglycemic Clamp study protocol in T2DM subjects according to a further embodiment of the present invention.
Figure 7B:
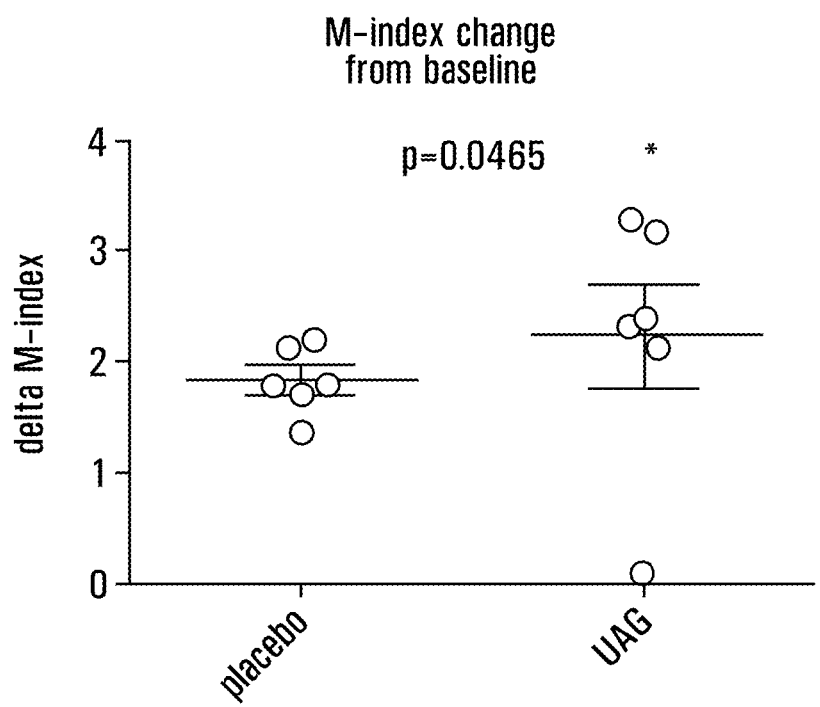
FIG. 7B is a graph illustrating the effects of UAG on the M-index, reflective of insulin sensitivity, during the protocol as schematized in FIG. 7A. The change in M-index from baseline was measured following placebo and UAG infusions. *: p<0.05, One-tailed Mann Whitney test.

Insulin sensitivity in T2DM subjects was assessed using the hyperinsulinemic-euglycemic clamp protocol as depicted in FIG. 7A. In patients receiving effective euglycemic insulin clamp at the start of a 2.5 hr placebo/UAG infusion, the M-index change from baseline was increased by 36% in the UAG vs. placebo group (p=0.02) (FIG. 7B). These results demonstrate that UAG infusion improves insulin resistance in T2DM subjects.

Shorter UAG Infusion is Sufficient to Decrease Plasma AG Levels

Figure 7C:
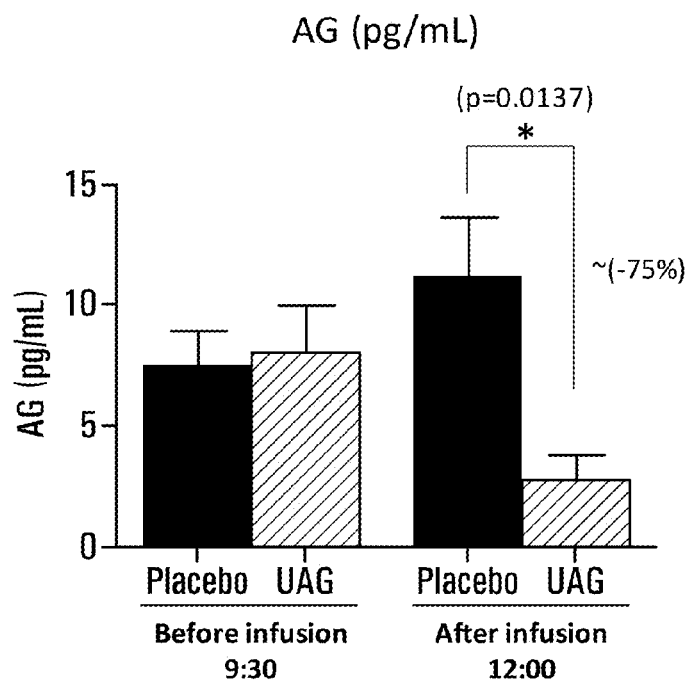
FIGS. 7C and 7D are graphs illustrating the effects of a short UAG infusion period on basal AG levels in T2DM subjects.
Figure 7D:
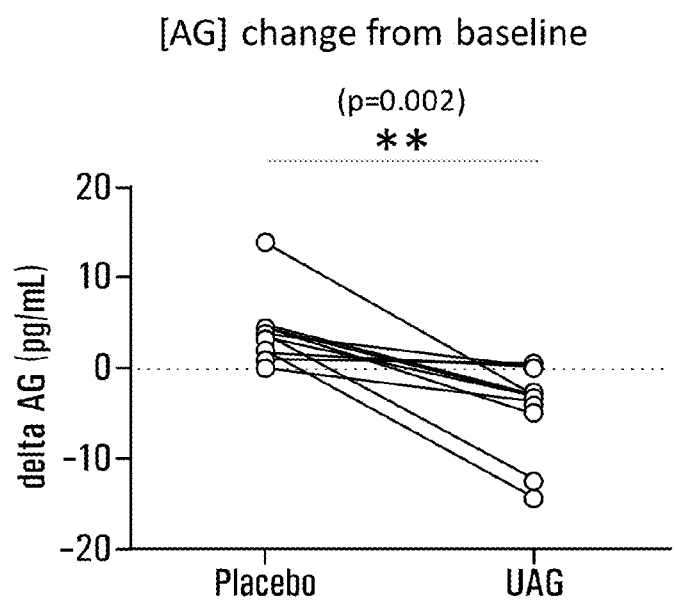

AG levels were measured in T2DM subjects prior to UAG infusion and following a 2.5 hour-long UAG infusion. The data presented in FIG. 7C shows that the shortened UAG infusion period was sufficient to decrease plasma AG levels. FIG. 7D indicates the changes in AG levels from baseline demonstrating that a short UAG infusion period suffices to decrease plasma AG levels.

These data demonstrate, inter alia, that administration of UAG improves glucose levels during a SBM through a reduction in AG. A significant decrease in peak glucose levels after meal was also observed. No significant change in serum insulin levels during the infusion of low and high dose of UAG infusions was observed (data not shown), which indicates that the improved glycemic control correlates with an improved insulin sensitivity. The data also show that administration of UAG improves hyperglycemia in a ghrelin concentration dependent manner thus making the UAG hypoglycemic effects stronger at higher AG levels or at higher AG/UAG ratio.

These results are the first indication that UAG is a potent inhibitor of ghrelin levels making UAG a strong candidate for the development of a ghrelin inhibitor in the treatment of metabolic disorders.

Materials and Technical Protocols

Study Design

Single-center, investigator initiated, double blind and placebo controlled randomized study. During the first visit medical history, medication use and vital signs of subjects were checked. Blood samples were also taken for chemistry and hematology analysis. The study consisted of three rounds of hospitalization (visit 2, 3 and 4) of two days each.

The first day started at approximately 15:00 and continued until 14:00 the next day. The eight subjects were divided into 3 groups for the study. The dosages used during these rounds were either 3 mcg/kg·hr UAG, 10 mcg/kg·hr UAG or placebo/saline solution prepared by the hospital pharmacy and delivered in 3 bags for each subject. Neither subjects nor researchers were aware of the drug given in these rounds. A washout period of one week was performed between the treatment periods.

Before, during and after the study, blood samples were taken for, AG, UAG, chemistry, hematology and CAC cells. Blood samples for glucose were also taken via i.v catheter. For continuous glucose monitoring a Continuous Glucose monitor (iPro2, Medtronic trading, The Netherlands) was placed in the abdomen of the subjects. Weight and blood pressure were measured during each visit. A washout period of at least 1 week was performed between the treatment periods.

Subjects

Eight subjects were enrolled (2 females and 6 males; mean age of 53 yrs (ranging from 31-65 years old) with mean body mass index (BMI) of 31.5 kg/m$^2$, range 26-36 kg/m$^2$. Seven of the eight subjects used metformin daily. All subjects were diagnosed with type 2 diabetes for at least 3 months prior to enrollment. Metformin monotherapy for at least 3 months prior to screening was allowed, but metformin treatment was stopped 1 day prior to start of each treatment period. In the population mean glycosylated hemoglobin level (HbA1c) was 52 mmol/mol range from 48 mmol/mol to 57 mmol/mol (6.9%; range 6.5-7.4%).) and Body Mass Index was above 25 kg/m$^2$. Exclusion criteria consisted in history or presence of long-term type 2 diabetes complications; clinically significant abnormalities in laboratory evaluation at screening, and use of systemic corticosteroids within 60 days prior to screening. Prior to infusion, subjects received two indwelling catheters: the first catheter was inserted prior to treatment; and the second catheter was inserted prior to the SBM for blood sampling. The second catheter was kept patent by slow infusion of isotonic saline.

Study Drug

UAG used in this study was produced by Bachem AG, Hauptstrasse 144, Bubendorf CH-4416, Switzerland. UAG was delivered as lyophilized powder (vials containing 5 mg of drug) and stored at the local pharmacy according to the manufacturer's specifications.

Study Procedures

Infusions were performed at the local clinical research unit for 15 hours from 9 pm to 12 am. Each volume of UAG solution was filtered and diluted in 0.9% of saline solution to obtain the appropriate dose for administration. Placebo consisted in 0.9% of saline solution. The dose was calculated based on the subject's weight. Each vial was reconstituted with 5 ml water for injection, filtered through a 0.22 µm filter. The dose was then injected in a 500 ml bag of 0.9% NaCl. Three bags were prepared to ensure a continuous 15-hour infusion at 100 ml/hour.

Standard breakfast meal (SBM) consisted of:
3 slices wheat bread;
3 portions of margarine;
2 slices of cheese (48% fat);
1 portion of jam;
1 cup of whole milk; and
1 boiled egg;

for a total of 714 kcal (17% proteins; 46% fat; and 37% carbohydrates). The SBM had to be consumed within 15 minutes, from 8:00 am to 8:15 am. At each of the 3 visits, the following safety parameters were assessed: hemoglobin, hematocrit, platelet count, WBC count, RBC count, and differential and were determined using Sysmex XE 2100, Firma Sysmex, Ecustraat 11, 4879 NP Etten-Leur. AST, ALT, alkaline phosphatase, total bilirubin, creatine phophokinase (CPK), lactate dehydrogenase (LDH), creatinine, urea, amylase, lipase, uric acid, glucose, cholesterol, LDL, HDL, triglycerides, sodium, potassium, calcium, chloride, protein and albumin are determined using the Hitachi Modular P800, Roche Transistorstraat 41, 1332 CK Almere. Blood glucose levels were measured using a continuous glucose monitoring device (Medtronic CGMS iPro™ Continuous Glucose Recorder, Medtronic; The Netherlands) that was subcutaneously inserted for the whole treatment period. Serum glucose levels (using the in-house glucokinase assay) were also assessed every 30 minutes and starting before, and continuing for 4 hours after, the SBM. During the CGMS, all subjects had to perform at least four capillary glycemic tests per day. The data collected were entered into the CGMS monitor to obtain correlation coefficients between the SMBG and the CGMS values. All SMBG tests were performed using a digital glucometer (Contour, Bayer). AG and UAG levels were assessed before the start of the overnight infusion, 10 minutes before the start and 30 minutes after the SBM. To preserve acylation of ghrelin, blood samples were collected directly into EDTA tubes, then within 2 minutes 1 ml of EDTA-blood was added to 1 ml of preservative solution on ice (0.0295 N HCl containing 72 mM NaCl, 58 mM NaF, 4 mM 4-(2-Aminoethyl)benzenesulfonyl fluoride hydrochloride (a water soluble, irreversible serine protease inhibitor; AEBSF), pH 3.0, 295 mOsm/Kg Plasma was prepared by centrifugation at 4° C., then 1 ml was acidified with 100 µl 1N HCl and stored at −80° C. until assays were performed.

The ghrelin assay utilized MSD ELISA 96-well plates (Meso Scale Discovery (MSD), Gaithersburg, Md., USA) coated by incubation with 30 µl/well of capture antibody (D4 diluted to 1 µg/ml in PBS; anti-C-terminal ghrelin (Gutierrez et al. 2008 PNAS 105:6320-6325)), overnight at room temperature. The capture antibody was removed and wells were blocked with 150 µl casein buffer (Pierce) for 1 h at room temperature with shaking. Standards for AG and UAG were prepared using eight 4× serial dilutions in casein buffer starting at 8 ng/ml and 30 ng/ml, respectively. Preserved plasma was diluted 1:1 in casein buffer. Separate plates were used for detection of AG and UAG. Standards and samples (25 µl/well) were loaded onto coated ELISA plates, and incubated at room temperature with shaking for 2 hours, washed 3× with PBS-T (150 µl/well). The C2-4a1 and E8 detection antibodies (N-terminal AG and N-terminal UAG, respectively) were sulfotagged using the standard protocol from MSD. They were then diluted 1:10000 in 0.2× casein/0.05% Tween 20 and added to AG or UAG plates, respectively, at 25 µl/well. Plates were incubated at room temperature for 1 hour with shaking. Plates were washed three times with PBS-T (150 µl/well). Finally, 150 µl of 1× Read Buffer (MSD) was added to each well, and the plates were immediately read on an MSD Sector Imager 6000. AG and UAG values for samples were calculated by interpolation from their respective standard curves using Sector Imager software.

Clamp Study

Randomized 2-period, 2-treatment, double-blind study of UAG vs. vehicle infusion, evaluating one dose (10 µg/kg/h) of UAG administered by continuous iv infusion for 2.5 hrs. In patients receiving effective euglycemic insulin clamp at the start of a 2.5 hr placebo/UAG infusion.

Statistical Analyses

Data analyses were performed with the GraphPad Prism 5.0 (GraphPad Software, Inc. La Jolla, Calif. 92037 USA). The results are given as means (±SE). Comparisons were calculated using Bonferroni's Multiple Comparisons, Wilcoxon matched-pairs signed-rank tests and ANOVA analyses.

With respect to the experimental data presented in FIG. 8, Sprague-Dawley rats of 7 weeks of age, weighing between 275 g and 300 g, were fed a pellet diet ad libitum and were singly housed in plastic cage. The experiment was performed at 2.5 h after the onset of the light cycle in freely fed rats. The rates were i.p. injected simultaneously with vehicle plus vehicle, vehicle+AG (13 µg/kg) or cyclised UAG (6-13) (SEQ ID NO: 25) (42 µg/kg)+AG (13 µg/kg). Immediately after the completion of the i.p. injection in rats, the night-ad-libitum food was removed and replaced by 2 pellets for each animal, previously weighed, placed into the top of the cage. Food intake was calculated as the difference between the food weight before and after the feeding period at each time interval (30 min, 1 h, and 2 h). Cumulative food intake was calculated by summating the values of the different time periods.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

All documents mentioned in the specification are herein incorporated by reference.

REFERENCE LIST

1. Kojima M, Hosoda H, Date Y, Nakazato M, Matsuo H and. Kangawa K; Ghrelin is a growth-hormone-releasing acylated peptide from stomach, Nature 402:656-660 (1999).
2. Gnanapavan S, Kola B, Bustin S A, Morris D G, McGee P, Fairclough P, Bhattacharya S, Carpenter R, Grossman A B and Korbonits M; The tissue distribution of the mRNA of ghrelin and subtypes of its receptor, GHS-R, in humans, J. Clin. Endocrinol. Metab. 87:2988-2991 (2002).
3. Howard A D, Feighner S D, Cully D F, Arena J P, Liberator P L, Rosenblum C I, Hamelin M, Hreniuk D L, Palyha O C, Anderson J, Paress P S, Diaz C, Chou M, Liu K K, McKee K-K, Pong S-S, Chaung L-Y, Elbrecht A, Dashkevicz M, Heavens R, Rigby M, Sirinathsinghji D, Dean D C, Melillo D G, Patchett A A, Nargund R, Griffin P R, DeMartino J A, Gupta S K, Schaeffer J A, Smith R G, Van der Ploeg L H T; A receptor in pituitary and hypothalamus that functions in growth hormone release. Science 273:974-977 (1996).
4. Ariyasu H, Takaya K, Tagami T, Ogawa Y, Hosoda K, Akamizu T, Suda M, Koh T, Natsui K, Toyooka S, Shirakami G, Usui T, Shimatsu A, Doi K, Hosoda H, Kojima M, Kangawa K, Nakao K.; Stomach is a major source of circulating ghrelin, and feeding state determines plasma ghrelin-like immunoreactivity levels in humans. J Clin Endocrinol Metab. October; 86(10):4753-8 (2001)
5. Date Y, Murakami N, Toshinai K, Matsukura S, Niijima A, Matsuo H, Kangawa K, Nakazato M. The role of the gastric afferent vagal nerve in ghrelin-induced feeding and growth hormone secretion in rats. Gastroenterology 123(4):1120-1128, 2002.
6. Kojima M, Hosoda H, Date Y, Nakazato M, Matsuo H, Kangawa K. Ghrelin is a growth-hormone-releasing acylated peptide from stomach. Nature 402(6762):656-660, 1999.
7. Tschop M, Smiley D L, Heiman M L. Ghrelin induces adiposity in rodents. Nature 407(6806):908-913, 2000.
8. Broglio F, Gianotti L, Destefanis S, Fassino S, Abbate Daga G, Mondelli V, Lanfranco F, Gottero C, Gauna C, Hofland L, Van Der Lely A J, Ghigo E. The endocrine response to acute ghrelin administration is blunted in patients with anorexia nervosa, a ghrelin hypersecretory state. Clin Endocrinol (Oxf) 60(5):592-599, 2004.
9. Tong J, Prigeon R L, Davis H W, Bidlingmaier M, Kahn S E, Cummings D E, Tschop M H, D'Alessio D. Ghrelin suppresses glucose-stimulated insulin secretion and deteriorates glucose tolerance in healthy humans. Diabetes September; 59(9):2145-51 (2010).
10. Cummings D E, Clement K, Purnell J Q, Vaisse C, Foster K E, Frayo R S, Schwartz M W, Basdevant A, Weigle D S. Elevated plasma ghrelin levels in Prader Willi syndrome. Nat Med 8(7):643-644 (2002).
11. Haqq A M F, Farooqi I S, O'Rahilly S, Stadler D D, Rosenfeld R G, Pratt K L, Lafranchi S H, Purnell J Q. Serum ghrelin levels are inversely correlated with body mass index, age, and insulin concentrations in normal children and are markedly increased in Prader-Willi syndrome. J Clin Endocrinol Metab 88(1):174-178 (2003).
12. Mifune H, Nishi Y, Tajiri Y, Masuyama T, Hosoda H, Kangawa K, Kojima M. Increased production of active ghrelin is relevant to hyperphagia in nonobese spontaneously diabetic Torii rats. Metabolism. 2011 Oct. 14. [Epub ahead of print]
13. Misra M, Miller K K, Kuo K, Griffin K, Stewart V, Hunter E, Herzog D B, Klibanski A. Secretory dynamics of ghrelin in adolescent girls with anorexia nervosa and healthy adolescents. Am J Physiol Endocrinol Metab 289(2):E347-E356 (2005).
14. Nikolopoulos D, Theocharis S, Kouraklis G. Ghrelin: a potential therapeutic target for cancer. Regul Pept 163(1-3):7-17 (2010).
15. van der Lely A J, Tschop M, Heiman M L, Ghigo E; Biological, physiological, pathophysiological, and pharmacological aspects of ghrelin. Endocr Rev 25:426-457 (2004).
16. Asakawa A, Inui A, Fujimiya M, Sakamaki R, Shinfuku N, Ueta Y, Meguid M M, Kasuga M. Stomach regulates energy balance via acylated ghrelin and desacyl ghrelin. Gut. January; 54(1):18-24 (2005).
17. Zhang W, Chai B, Li J Y, Wang H, Mulholland M W. Effect of des-acyl ghrelin on adiposity and glucose metabolism. Endocrinology. September; 149(9):4710-6. (2008)
18. Broglio F, Gottero C, Prodam F, Gauna C, Muccioli G, Papotti M, Abribat T, Van Der Lely A J, Ghigo E. Non-acylated ghrelin counteracts the metabolic but not the neuroendocrine response to acylated ghrelin in humans. J Clin Endocrinol Metab. June; 89(6):3062-5 (2004).
19. Gauna C, Meyler F M, Janssen J A, Delhanty P J, Abribat T, van Koetsveld P, Hofland L J, Broglio F, Ghigo E, van der Lely A J. Administration of acylated ghrelin reduces insulin sensitivity, whereas the combination of acylated plus unacylated ghrelin strongly improves insulin sensitivity. J Clin Endocrinol Metab. October; 89(10):5035-42 (2004).
20. St-Pierre D H, Karelis A D, Coderre L, Malita F, Fontaine J, Mignault D, Brochu M, Bastard J P, Cianflone K, Doucet E, Imbeault P, Rabasa-Lhoret R. Association of acylated and nonacylated ghrelin with insulin sensitivity in overweight and obese postmenopausal women. J Clin Endocrinol Metab. January; 92(1):264-9 (2007).
21. Pacifico L, Poggiogalle E, Costantino F, Anania C, Ferraro F, Chiarelli F, Chiesa. Acylated and nonacylated ghrelin levels and their associations with insulin resistance in obese and normal weight children with metabolic syndrome. Eur J Endocrinol. December; 161(6):861-70 (2009).
22. Barazzoni R, Zanetti M, Ferreira C, Vinci P, Pirulli A, Mucci M, Dore F, Fonda M, Ciocchi B, Cattin L, Guarnieri G. Relationships between desacylated and acylated ghrelin and insulin sensitivity in the metabolic syndrome. J Clin Endocrinol Metab. October; 92(10):3935-40 (2007).
23. Rodríguez A, Gómez-Ambrosi J, Catalán V, Gil M J, Becerril S, Sáinz N, Silva C, Salvador J, Colina I, Frühbeck G. Acylated and desacyl ghrelin stimulate lipid accumulation in human visceral adipocytes. Int J Obes (Lond). May; 33(5):541-52 (2009).
24. Schellekens H, Dinan T G, Cryan J F. Lean mean fat reducing "ghrelin" machine: Hypothalamic ghrelin and ghrelin receptors as therapeutic targets in obesity. Neuropharmacology 58(1):2-19 (2010).
25. Gualillo O, Lago F, Dieguez C. Introducing GOAT: a target for obesity and anti-diabetic drugs? Trends Pharmacol Sci 29(8):398-401 (2008).
26. Hillman J B, Tong J, Tschop M. Ghrelin biology and its role in weight-related disorders. Discov Med. June; 11(61):521-8 (2011).
27. Kumar R, Salehi A, Rehfeld J F, Höglund P, Lindström E, Håkanson R. Proghrelin peptides: Desacyl ghrelin is a powerful inhibitor of acylated ghrelin, likely to impair physiological effects of acyl ghrelin but not of obestatin A study of pancreatic polypeptide secretion from mouse islets. Regul Pept. September 24; 164(2-3):65-70 (2010)
28. Cummings D E, Weigle D S, Frayo R S, Breen P A, Ma M K, Dellinger E P, Purnell J Q. Plasma ghrelin levels after diet-induced weight loss or gastric bypass surgery. N Engl J Med. May 23; 346(21):1623-30 (2002).
29. Sumithran P, Prendergast L A, Delbridge E, Purcell K, Shulkes A, Kriketos A, Proietto J. Long-term persistence of hormonal adaptations to weight loss. N Engl J Med. October 27; 365(17):1597-604 (2011).
30. Kiewiet R M, van Aken M O, van der Weerd K, Uitterlinden P, Themmen A P, Hofland L J, de Rijke Y B, Delhanty P J, Ghigo E, Abribat T, van der Lely A J. Effects of acute administration of acylated and unacylated ghrelin on glucose and insulin concentratios in morbidly obese subjects without overt diabetes. Eur J Endocrinol 161: 567-573 (2009).
31. Gauna C, Delhanty P J D, Hofland L J, Janssen J, Broglio F, Ross R J M, Ghigo E, van der Lely A J. Ghrelin stimulates, whereas des-octanoyl ghrelin inhibits, glucose output by primary hepatocytes. Journal of Clinical Endocrinology and Metabolism 90:1055-1060 (2005).
32. Gauna C, Kiewiet R M, Janssen J A, van de Zande B, Delhanty P J, Ghigo E, Hofland L J, Themmen A P, van der Lely A J. Unacylated ghrelin acts as a potent insulin secretagogue in glucose-stimulated conditions. Am J Physiol Endocrinol Metab 293:E697-704 (2007).

33. Granata R, Settanni F, Gallo D, Trovato L, Biancone L, Cantaluppi V, Nano R, Annunziata M, Campiglia P, Arnoletti E, Ghe C, Volante M, Papotti M, Muccioli G, Ghigo E. Obestatin promotes survival of pancreatic beta-cells and human islets and induces expression of genes involved in the regulation of beta-cell mass and function. Diabetes 57:967-979 (2008).

34. Longo K A, Charoenthongtrakul S, Giuliana D J, Govek E K, McDonagh T, Qi Y, DiStefano P S, Geddes B J. Improved insulin sensitivity and metabolic flexibility in ghrelin receptor knockout mice. Regul Pept 150:55-61 (2008).

35. Nonogaki K, Nozue K, Oka Y. Hyperphagia alters expression of hypothalamic 5-HT2C and 5-HT1B receptor genes and plasma des-acyl ghrelin levels in Ay mice. Endocrinology 147:5893-5900 (2006).

36. Kitamura S, Yokota I, Hosoda H, Kotani Y, Matsuda J, Naito E, Ito M, Kangawa K, Kuroda Y. Ghrelin concentration in cord and neonatal blood: relation to fetal growth and energy balance. J Clin Endocrinol Metab. 2003 November; 88(11):5473-7.

The invention claimed is:

1. A method for treating Prader-Willi Syndrome in a subject, comprising administering to the subject an effective amount of (i) a polypeptide consisting of a fragment of unacylated ghrelin as set forth in SEQ ID NO: 6; (ii) a polypeptide consisting of a fragment of unacylated ghrelin as set forth in SEQ ID NO: 25; or (iii) pharmaceutically acceptable salts of (i) or (ii).

2. The method as defined in claim 1, wherein the effective amount is from about 0.001 µg/kg to about 10 µg/kg.

3. The method as defined in claim 1, wherein effective amount is from about 1 µg/kg to about 1 mg/kg.

* * * * *

UNITED STATES PATENT AND TRADEMARK OFFICE
CERTIFICATE OF CORRECTION

Page 1 of 1

PATENT NO. : 9,550,821 B2
APPLICATION NO. : 13/715550
DATED : January 24, 2017
INVENTOR(S) : Aart Jan Van Der Lely et al.

It is certified that error appears in the above-identified patent and that said Letters Patent is hereby corrected as shown below:

On the Title Page

Column 1, after Item (22), and before Prior Publication Data, please insert the following new paragraph:

-- Related U.S. Application Data
Provisional application no. 61/576,217, filed on December 15, 2011. --

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*